United States Patent
Qin et al.

(10) Patent No.: US 10,457,765 B2
(45) Date of Patent: Oct. 29, 2019

(54) METALLIC COMPLEX CATALYST, POLYMERIZATION METHODS EMPLOYING SAME AND POLYMER PRODUCTS THEREOF

(71) Applicant: Bridgestone Corporation, Chuo-ku (JP)

(72) Inventors: Zengquan Qin, Copley, OH (US); Joshua P. Abell, Nashville, TN (US)

(73) Assignee: Bridgestone Corporation, Chuo-ku (JP)

( * ) Notice: Subject to any disclaimer, the term of this patent is extended or adjusted under 35 U.S.C. 154(b) by 0 days.

(21) Appl. No.: 15/315,011

(22) PCT Filed: May 26, 2015

(86) PCT No.: PCT/US2015/032373
§ 371 (c)(1),
(2) Date: Nov. 30, 2016

(87) PCT Pub. No.: WO2015/183781
PCT Pub. Date: Dec. 3, 2015

(65) Prior Publication Data
US 2017/0114170 A1     Apr. 27, 2017

Related U.S. Application Data

(60) Provisional application No. 62/006,119, filed on May 31, 2014, provisional application No. 62/136,302, filed on Mar. 20, 2015.

(51) Int. Cl.
| | | |
|---|---|---|
| *C08F 236/06* | (2006.01) | |
| *C08F 4/52* | (2006.01) | |
| *C08F 4/54* | (2006.01) | |
| *C08F 4/6392* | (2006.01) | |
| *C07F 7/10* | (2006.01) | |
| *C08F 297/06* | (2006.01) | |
| *C08L 9/00* | (2006.01) | |
| *C07F 17/00* | (2006.01) | |

(52) U.S. Cl.
CPC ............ *C08F 236/06* (2013.01); *C07F 7/10* (2013.01); *C07F 17/00* (2013.01); *C08F 4/545* (2013.01); *C08F 4/6392* (2013.01); *C08F 297/06* (2013.01); *C08L 9/00* (2013.01); *C08F 2420/03* (2013.01); *C08F 2800/10* (2013.01); *C08F 2810/40* (2013.01)

(58) Field of Classification Search
CPC ...... C08F 236/06; C08F 36/06; C08F 297/06; C08F 2420/03; C08F 4/52; C08F 4/545; C08F 4/6392
See application file for complete search history.

(56) References Cited

U.S. PATENT DOCUMENTS

| | | |
|---|---|---|
| 6,569,799 B1 | 5/2003 | Barbotin et al. |
| 6,800,705 B2 | 10/2004 | Barbotin et al. |
| 7,094,854 B2 | 8/2006 | Monteil et al. |
| 7,300,903 B2 | 11/2007 | Fujita et al. |
| 7,547,654 B2 | 6/2009 | Boisson et al. |
| 8,524,793 B2 | 9/2013 | Peng et al. |
| 8,653,290 B2 | 2/2014 | Kaita et al. |
| 8,853,339 B2 | 10/2014 | Kaita et al. |
| 8,962,743 B2 | 2/2015 | Kaita et al. |
| 8,962,744 B2 | 2/2015 | Horikawa et al. |
| 8,969,496 B2 | 3/2015 | Kaita |
| 9,056,936 B2 | 6/2015 | Horikawa et al. |
| 9,074,035 B2 | 7/2015 | Kaita et al. |
| 9,181,376 B2 | 11/2015 | Horikawa et al. |
| 9,266,978 B2 | 2/2016 | Kaita et al. |
| 9,422,383 B2 | 8/2016 | LiPiShan et al. |
| 9,670,302 B2 | 6/2017 | Horikawa et al. |
| 9,701,776 B2 | 7/2017 | Horikawa et al. |
| 2012/0196993 A1* | 8/2012 | Kaita .................... C08F 210/02 526/126 |
| 2013/0316111 A1 | 11/2013 | Wu et al. |
| 2015/0210838 A1 | 7/2015 | Wu et al. |
| 2017/0073450 A1* | 3/2017 | Kimura .................... B60C 9/04 |
| 2017/0114171 A1 | 4/2017 | Abell et al. |

FOREIGN PATENT DOCUMENTS

| | | | |
|---|---|---|---|
| CN | 101220060 A | * | 7/2008 |
| JP | 2014-037499 A | | 2/2014 |

OTHER PUBLICATIONS

Xu et al., Chem. Eur. J. 15 (2009) 846-850.*
CN 101220060 A, machine translation of Description and Claims, Jul. 2008.*
First SIPO examination report, dated Feb. 2, 2018, in CN appl. No. 201580040332.5—original (9 pp.).
A. Davison et al, "Fluxional Behavior of Substituted Indenyl Derivatives of Silicon and Tin," J. Organometlic Chem., 1970, vol. 23, pp. 407-426 (Elsevier Sequoia S.A.; Netherlands).
D C. Bradley et al., "Three-co-ordination in Lanthanide Chemistry: Tris[bis(trimethylsilyl)amido]lanthanide(III) Compounds," J. Chem. Soc., Chem. Commun.,1972, pp. 349-350 (The Royal Society of Chemistry; London, England).

(Continued)

*Primary Examiner* — Roberto Rabago
(74) *Attorney, Agent, or Firm* — Meredith E. Hooker; David G. Burleson

(57) ABSTRACT

Metallic complexes having indenyl ligands can be used as an ingredient of a catalyst system. The catalyst system can be used in polymerizations of ethylenically unsaturated hydrocarbon monomers that include both olefins and polyenes. Embodiments of the catalyst system can provide interpolymers that include polyene mer and from 40 to 75 mole percent ethylene mer, with a plurality of the ethylene mer being randomly distributed. The catalyst system also can be used in solution polymerizations conducted in $C_5$-$C_{12}$ alkanes, yielding interpolymers that include at least 10 mole percent ethylene mer.

18 Claims, 9 Drawing Sheets

(56) References Cited

OTHER PUBLICATIONS

C.A. Bradley et al., "Synthesis and Characterization of Zirconium and Iron Complexes Containing Substituted Indenyl Ligands: Evaluation of Steric and Electronic Parameters," Organometallics, 2004, vol. 23, pp. 5332-5346 (American Chemical Society; Washington, DC).

J Thuilliez et al., "Alternating Copolymerization of Ethylene and Butadiene with a Neodymocene Catalyst," Angew. Chem. Int. Ed., 2005, vol. 44, pp. 2593-2396 (Wiley-VCH Verlag GmbH & Co.; Weinheim, Germany).

T.J. Woodman et al., "Heterogenized 'Ligand-Free' Lanthanide Catalysts for the Homo- and Copolymerization of Ethylene and 1,3-Butadiene," Macromolecules, 2005, vol. 38, pp. 3060-3067 (American Chemical Society; Washington, DC).

C. Capacchione et al., "Ethylene-Butadiene Copolymerization Promoted by Titanium Complex Containing a Tetradentate [OSSO]-Type Bis(phenolato) Ligand," Macromolecules, 2008, vol. 41, 4573-75 (American Chemical Society; Washington, DC).

C. Capacchione et al., "Copolymerization of Ethylene with Isoprene Promoted by Titanium Complexes Containing a Tetradentate [OSSO]-Type Bis(phenolato) Ligand," J. Polym. Sci.: A, 2010, vol. 48, pp. 4200-4206 (Wiley Periodicals, Inc.; Hoboken, NJ).

JPO examination report, dated Mar. 26, 2019, in JP appl. No. 2017-514996—original (5 pages) plus translation (6 pp.).

EPO examination report, dated Mar. 8, 2019, in EP appl. No. 15800182 (5 pp.).

Second CNIPA examination report, dated Dec. 21, 2018, in CN appl. No. 201580040332.5—original (6 pp.) plus translation (10 pp.).

First Russian Fed. examination report, dated Dec. 11, 2018, in RU appl. No. 2016147087—original (6 pp.) plus translation (5 pp.).

S. Pragliola et al., "Ethene/1,3-Butadiene Copolymerization in the Presence of rac-(CH2-(3-tert-butyl-1-indenyl)2) ZrCl2/MAO Catalytic System: Study of the Polymerization Mechanism by Using 13C-Labeled 1,3-Butadiene," Macromolecules, 2004, 37, pp. 238-240 (American Chemical Society; Washington, DC).

X. Xu et al., "Indenyl Abstraction versus Alkyl Abstraction of [(Indenyl)ScR2(thf)] by [Ph3C][B(C6F5)4]: Aspecific and Syndiospecific Styrene Polymerization," Chem. Eur. J., 2009, 15, pp. 846-850 (Wiley-VCH Verlag GmbH & Co. KGaA; Wernheim, Germany).

Chemical Abstracts document XP-002776968—S. Kniajanski, "Process for preparation of semi-crystalline poly(methyl methacrylate) with high melting temperature," MX patent appl. No. 2001-1160 filed Jan. 31, 2001 and published Aug. 5, 2002.

Chemical Abstracts document XP-002776969—S. Knajazhanski et al., "Stereospecific polymerization of methyl methacrylate with bis(indenyl)lanthanide complexes," Polymer Preprints, 2000, 41(2), pp. 1294-1295 (American Chemica Society; Washington, DC).

* cited by examiner

METALLIC COMPLEX CATALYST, POLYMERIZATION METHODS EMPLOYING SAME AND POLYMER PRODUCTS THEREOF

CROSS REFERENCE TO RELATED APPLICATIONS

This application is a national stage entry of international application no. PCT/US2015/032373, filed 26 May 2015, which claims the benefit of U.S. provisional appl. No. 62/006,119, filed 31 May 2014, and U.S. provisional patent appl. No. 62/136,302, filed 20 Mar. 2015, the disclosures of which are incorporated herein by reference.

BACKGROUND INFORMATION

Rubber goods such as tire treads often are made from elastomeric compositions that contain one or more reinforcing materials such as, for example, particulate carbon black and silica; see, e.g., *The Vanderbilt Rubber Handbook,* 13th ed. (1990), pp. 603-04.

Good traction and resistance to abrasion are primary considerations for tire treads; however, motor vehicle fuel efficiency concerns argue for a minimization in their rolling resistance, which correlates with a reduction in hysteresis and heat build-up during operation of the tire. Reduced hysteresis and traction are, to a great extent, competing considerations: treads made from compositions designed to provide good road traction usually exhibit increased rolling resistance and vice versa.

Filler(s), polymer(s), and additives typically are chosen so as to provide an acceptable compromise or balance of these properties. Ensuring that reinforcing filler(s) are well dispersed throughout the elastomeric material(s) both enhances processability and acts to improve physical properties. Dispersion of fillers can be improved by increasing their interaction with the elastomer(s), which commonly results in reductions in hysteresis (see above). Examples of efforts of this type include high temperature mixing in the presence of selectively reactive promoters, surface oxidation of compounding materials, surface grafting, and chemically modifying the polymer, typically at a terminus thereof.

Various natural and synthetic elastomeric materials often are used in the manufacture of vulcanizates such as, e.g., tire components. Some of the most commonly employed synthetic materials include high-cis polybutadiene, often made by processes employing catalysts, and substantially random styrene/butadiene interpolymers, often made by processes employing free radical or anionic initiators.

Of particular difficulty to synthesize are interpolymers of olefins and polyenes, particularly conjugated dienes, due in large part to the very different reactivities of those two types of ethylenically unsaturated monomers. Their respective susceptibilities to coordinate with the metal atoms of polymerization catalysts differ greatly.

Although difficult to synthesize, such interpolymers are of significant commercial interest. Because polyene and olefin monomers usually originate from different raw materials and are provided via different techniques, manufacturers of elastomeric materials can guard against supply and price disruptions of either monomer by synthesizing interpolymers with varying and/or adjustable amounts of mer from each.

Additionally, certain portions of pneumatic tires, particularly sidewalls, preferably exhibit good resistance to atmospheric degradation, particularly ozone degradation. Such components can benefit from inclusion of substantially saturated elastomer(s). Historically, typical options have included ethylene/propylene/non-conjugated diene (EPDM) interpolymers or brominated copolymers of isobutylene and para-methylstyrene. Alternatives to these materials also remain desirable.

SUMMARY

Any of a class of indenyl-metal complexes can be used as an ingredient of a catalyst system. The catalyst system can be used in polymerizations of ethylenically unsaturated hydrocarbon monomers, including mixtures or blends of polyenes and olefins.

The class of metallic complexes can be represented by the general formula

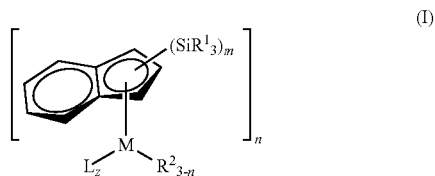

where M represents a Group 3 metal atom; L represents a neutral Lewis base; z is an integer of from 0 to 3 inclusive; m is 1 or 2 with the proviso that, when m=2, the silyl groups are at the 1 and 3 positions of the indenyl ligand; n is 1 or 2; each $R^1$ independently is H, a halogen atom, a $C_1$-$C_{20}$ alkyl group, a $C_5$-$C_8$ cycloalkyl group, an aralkyl group, an alkoxy group, a siloxy group, a nitro group, a sulfonate group, or a —$(CH_2)_y R^3$ group where y is 0 or 1 and $R^3$ is a substituted or unsubstituted aryl group; and $R^2$ is an X-type, monoanionic ligand. An L group and an $R^2$ group optionally can join so as to provide, together with the M atom to which each is bonded, a cyclic moiety. Alternatively or additionally, two $R^1$ groups can join to form a substituted or unsubstituted hydrocarbylene group that, together to the Si atom, can form a cyclic moiety.

Aspects of the invention include a catalyst composition that includes the formula (I) complex, certain of which also involve a catalyst activator, as well as methods of making both the complex and the catalyst composition.

In a further aspect is provided a process of polymerizing ethylenically unsaturated hydrocarbon monomers which involves contacting the monomers with the aforedescribed catalyst composition. The ethylenically unsaturated hydrocarbon monomers can include one or more types of polyene, including dienes, and, in some embodiments, the resulting diene mer advantageously can incorporate preferentially in a 1,4-configuration, i.e., the polymer product can have low amounts of vinyl mer. The ethylenically unsaturated hydrocarbon monomers also can include one or more types of olefin and, in some embodiments, the resulting polymer can include large amounts of olefin mer (e.g., at least about 50 mole percent) which, in many embodiments, can be incorporated substantially random throughout the polymer chain or, in other embodiments, can be present in a block of randomly distributed olefin and polyene mer. In certain embodiments, the process can be conducted in a solvent system that is primarily, or even completely, composed of $C_5$-$C_{10}$ alkanes. In these and other embodiments, the process optionally can include providing the resulting polymer with a terminal moiety that includes one or more heteroatoms, a step that can enhance the ability of a polymer to interact with a variety of types of particulate fillers.

In yet another aspect is provided a polyene/olefin interpolymer that includes a high amount of olefin mer. When the olefin is or includes ethylene, the interpolymer can contain from ~40 to ~75 mole percent ethylene mer, with a plurality of such ethylene mer being randomly distributed. Additionally, when the polyene is a conjugated diene, at least 40%, at least 45% or even at least 50% of the conjugated diene mer, relative to the total moles of diene mer, can have a cis isomeric configuration. In some embodiments, the polyene/olefin interpolymer can include at least one block of polyene mer and a block of randomly distributed polyene and olefin mer. A particular embodiment of this aspect is a conjugated diene/ethylene copolymer wherein one block has conjugated diene mer having the amount of cis isomeric configuration described above and another block having randomly distributed conjugated diene and ethylene mer.

In a still further aspect is provided a composition that includes an interpolymer in a solvent system that includes at least 50 weight percent of one or more $C_5$-$C_{10}$ alkanes and, in some embodiments, includes only such $C_5$-$C_{10}$ alkanes. The interpolymer component includes polyene mer and at least 10 mole percent ethylene mer. A plurality of the ethylene mer can be randomly distributed in the interpolymer.

The foregoing polymerization processes also optionally can include providing the resulting polymer with a terminal moiety that includes one or more heteroatoms so as to enhance the ability of the polymer to interact with a variety of types of particulate filler such as, e.g., carbon black and/or silica.

Also provided are compositions, including vulcanizates, that include particulate fillers and the resulting polymers, certain embodiments of which may also include terminal functionality, as are methods of providing and using such compositions.

Other aspects of the invention will be apparent to the ordinarily skilled artisan from the detailed description that follows. To assist in understanding that description, certain definitions are provided immediately below, and these are intended to apply throughout unless the surrounding text explicitly indicates a contrary intention:

"polymer" means the polymerization product of one or more monomers and is inclusive of homo-, co-, ter-, tetra-polymers, etc.;

"mer" and "mer unit" both mean that portion of a polymer derived from a single reactant molecule (e.g., ethylene mer has the general formula —$CH_2CH_2$—);

"copolymer" means a polymer that includes mer units derived from two reactants, typically monomers, and is inclusive of random, block, segmented, graft, etc., copolymers;

"interpolymer" means a polymer that includes mer units derived from at least two reactants, typically monomers, and is inclusive of copolymers, terpolymers, tetrapolymers, and the like;

"substituted" means containing a heteroatom or functionality (e.g., hydrocarbyl group) that does not interfere with the intended purpose of the group in question;

"polyene" means a molecule, typically a monomer, with at least two double bonds located in the longest portion or chain thereof, and specifically is inclusive of dienes, trienes, and the like;

"polydiene" means a polymer that includes mer units from one or more dienes;

"lanthanide metal" means any element having an atomic number of 57-71 inclusive;

"Group 3 metal" means Sc, Y or a lanthanide series metal;

"phr" means parts by weight (pbw) per 100 pbw rubber;

"radical" means the portion of a molecule that remains after reacting with another molecule, regardless of whether any atoms are gained or lost as a result of the reaction;

"neutral Lewis base" means a non-ionic compound (or radical) that includes an available pair of electrons;

"aryl" means a phenyl or polycyclic aromatic radical;

"aralkyl" means an alkyl radical that includes an aryl substituent, e.g., a benzyl group;

"non-coordinating anion" means a sterically bulky anion that does not form coordinate bonds with, for example, the active center of a catalyst system due to steric hindrance;

"non-coordinating anion precursor" means a compound that is able to form a non-coordinating anion under reaction conditions;

"terminus" means an end of a polymeric chain;

"terminally active" means a polymer with a living or pseudo-living terminus; and "terminal moiety" means a group or functionality located at a terminus.

Throughout this document, all values given in the form of percentages are weight percentages unless the surrounding text explicitly indicates a contrary intention. The relevant portion(s) of any specifically referenced patent and/or published patent application are incorporated herein by reference.

DETAILED DESCRIPTION OF ILLUSTRATIVE EMBODIMENTS

Figure 1:
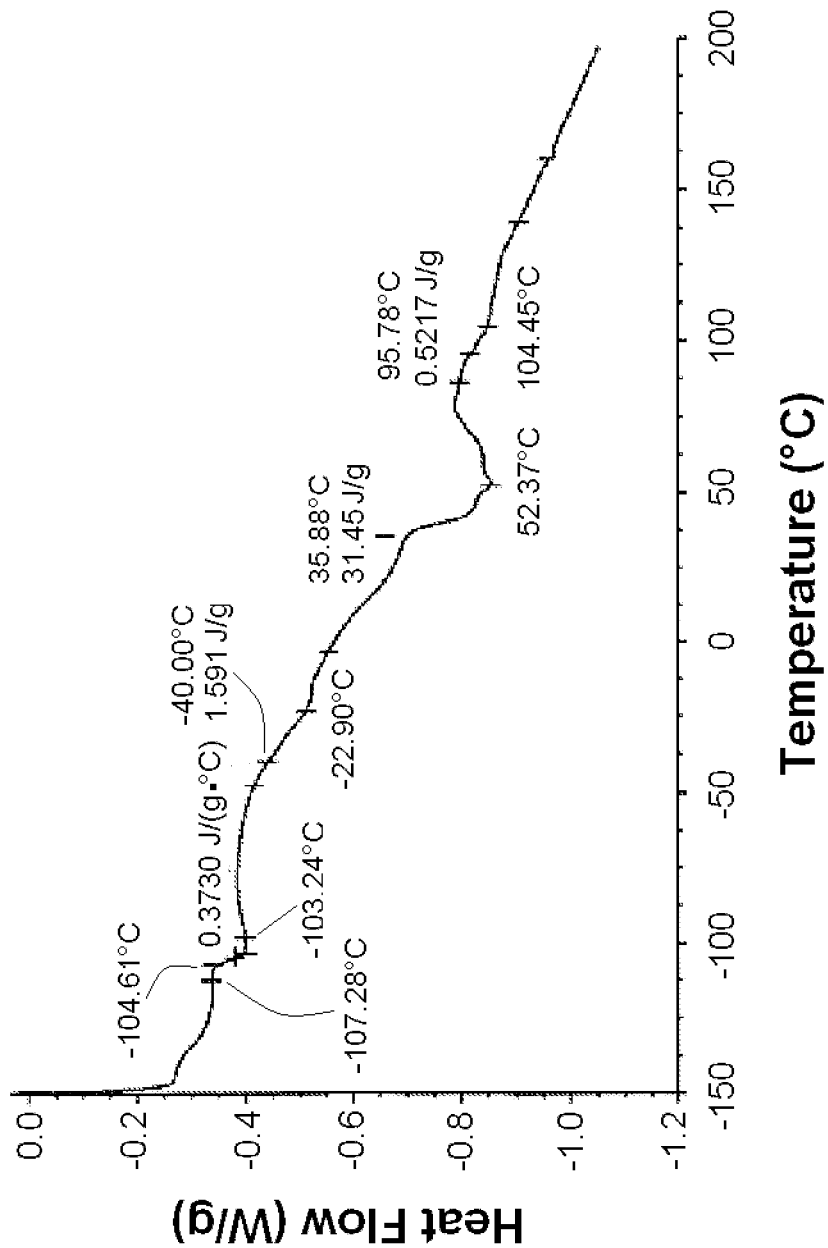
FIG. 1 is a heat flow vs. temperature plot obtained by differential scanning calorimetry (DSC) on the polymer from Example 3.

As apparent from the foregoing, the catalyst composition can be used to polymerize one or more types of polyenes, optionally but in some respects preferably in combination with one or more types of olefins.

The resulting polymer can be elastomeric, including mer that themselves include ethylenic unsaturation. Mer units that include ethylenic unsaturation can be derived from polyenes, particularly dienes and trienes (e.g., myrcene). Illustrative polyenes include $C_4$-$C_{30}$ dienes, preferably $C_4$-$C_{12}$ dienes. Preferred among these are conjugated dienes such as, but not limited to, 1,3-butadiene, 1,3-pentadiene, 1,3-hexadiene, 1,3-octadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, 2,4-hexadiene, and the like.

Polymers having overall 1,2-microstructures of no more than 50%, preferably no more than 35%, based on total moles of polyene mer is considered to be "substantially linear." Certain end use applications argue for even lower amounts of 1,2-linkages, e.g., less than 20%, less than 15%, or even less than 10%. The present catalyst compositions have been found to be capable of providing polymers that have from ~2 to ~10% 1,2-linkages.

Those polyene mer not incorporating into a polymer chain in a vinyl (1,2-) configuration can have either a cis or trans isomeric configuration. Polymers that have high cis-1,4-linkage contents are desirable for certain end use applications but can be difficult or inefficient to achieve via free radical or anionic (living) polymerizations. Polymers with high amounts of cis-1,4 diene mer, therefore, commonly are prepared by processes using selective catalysts.

The present process can provide polymers with polydiene mer having a cis-1,4-linkage content of ~40% to ~70%, typically ~45% to ~60%, with each of the foregoing representing a numerical percentage relative to total number of mer. While these percentages are not as high as seen in polymers prepared using other catalyst systems, the polymers that result from the present process have other characteristics not previously obtainable via previously known processes.

Examples of olefins that can be employed in the polymerization process include $C_2$-$C_{30}$, preferably $C_2$-$C_{20}$ and more preferably $C_2$-$C_{12}$, straight chain or branched $\alpha$-olefins such as ethylene, propylene, 1-butene, 1-pentene, 3-methyl-1-butene, 1-hexene, 4-methyl-1-pentene, 3-methyl-1-pentene, 1-octene, 1-decene, 1-dodecene, 1-tetradecene, 1-hexadecene, 1-octadecene, 1-eicosene, and the like, as well as $C_3$-$C_{30}$ cycloolefins such as cyclopentene, cycloheptene, norbornene, 5-methyl-2-norbornene, and tetracyclododecene. In several embodiments, ethylene constitutes a preferred olefin.

The polymerization process can provide olefin/polyene interpolymers having a wide range of amounts of each type of mer, i.e., embodiments of the process employing certain formula (I)-type complexes in a catalyst system can result in interpolymers having predominant amounts of polyene mer, e.g., olefin/conjugated diene copolymers that include more conjugated diene mer than olefin mer, while embodiments of the process employing catalyst systems that involve certain other formula (I)-type complexes can result in interpolymers having predominant amounts of olefin mer. Resulting interpolymers can contain at least 10, 20, 30, 40, 50, 60 or even up to 70% olefin mer, even where the interpolymers are prepared in solvent systems that contain predominantly or only $C_5$-$C_{10}$ alkanes. (All of the foregoing percentages are mole percents, and it is envisioned to combine these percentages into pairs so as to form ranges, e.g., at least 10 to 70%, at least 10 to 60%, at least 20 to 70%, etc.)

The number average molecular weight ($M_n$) of a polymer produced according to the disclosed methods typically is such that a quenched sample exhibits a gum Mooney viscosity ($ML_{1+4}/100°$ C.) of from ~2 to ~150, more commonly from ~2.5 to ~125, even more commonly from ~5 to ~100, and most commonly from ~10 to ~75; the foregoing generally corresponds to a $M_n$ of from ~5,000 to ~250,000 Daltons, commonly from ~10,000 to ~150,000 Daltons, more commonly from 50,000 to ~120,000 Daltons, and most commonly from ~10,000 to ~100,000 Daltons or even ~10,000 to ~80,000 Daltons. The resulting interpolymer typically has a molecular weight distribution ($M_w/M_n$) of from 1 to 20, commonly from 2 to 15, and more commonly from 3 to 10. (Both $M_n$ and $M_w$ can be determined by GPC using polystyrene standards for calibration.)

The foregoing types of polymers can be made by solution polymerization, which affords exceptional control of properties as randomness, microstructure, etc. Solution polymerizations have been performed since about the mid-20th century, so the general aspects thereof are known to the ordinarily skilled artisan; nevertheless, certain aspects are provided here for convenience of reference.

Suitable solvents include those organic compounds that do not undergo polymerization or incorporation into propagating polymer chains (i.e., are inert toward and unaffected by the catalyst composition) and preferably are liquid at ambient temperature and pressure. Examples of suitable organic solvents include hydrocarbons with relatively low boiling points such as aromatic hydrocarbons including benzene and toluene as well as (cyclo)aliphatic hydrocarbons such as, e.g., cyclohexane. Exemplary polymerization solvents also include various $C_5$-$C_{12}$ cyclic and acyclic alkanes (e.g., n-pentane, n-hexane, n-heptane, n-octane, n-nonane, n-decane, isopentane, isohexanes, isooctanes, 2,2-dimethylbutane, cyclopentane, cyclohexane, methylcyclopentane, methylcyclohexane, etc.) as well as their alkylated derivatives, certain liquid aromatic compounds (e.g., benzene, toluene, xylenes, ethylbenzene, diethylbenzene, and mesitylene), petroleum ether, kerosene, petroleum spirits, and mixtures thereof. Other potentially suitable organic compounds that can be used as solvents include high-boiling hydrocarbons of high molecular weights such as paraffinic oil, aromatic oil, or other hydrocarbon oils that are commonly used to oil-extend polymers. The ordinarily skilled artisan is aware of other useful solvent options and combinations.

Advantageously, in certain embodiments, a solution polymerization can be performed in a solvent system that includes at least 50% (by wt.) of one or more $C_5$-$C_{10}$ alkanes, preferably $C_5$-$C_{10}$ linear alkanes. In certain of these embodiments, the solvent system can include only such $C_5$-$C_{10}$ linear alkanes. Advantageously, embodiments of the polymerization process conducted in a solvent system that is mostly or only $C_5$-$C_{10}$ linear alkanes can yield polymers having high levels of olefin mer, e.g., a diene/ethylene interpolymer having at least 10, at least 15, at least 20, at least 25, at least 33, at least 40 or even at least 50 mole percent ethylene mer.

As described previously, the polymerization process employs a catalyst composition that includes a particular class of Group 3 metal complexes. The term "catalyst composition" encompasses a simple mixture of ingredients, a complex of various ingredients that results from physical or chemical forces of attraction, a chemical reaction product of some or all of the ingredients, or a combination of the foregoing.

Exemplary catalyst compositions include (a) a formula (I) complex, an alkylating agent and optionally a halogen-containing compound (where neither the formula (I) complex or the alkylating agent contains a halogen atom); (b) a formula (I) complex and an aluminoxane; or (c) a formula (I) complex, an alkylating agent, and a non-coordinating anion or precursor thereof. Certain embodiments of a formula (I) complex might be able to be used alone as a catalyst. Each component of these exemplary compositions is discussed separately below.

The polymerization processes described herein employ a specific genus of Group 3 metal complexes, specifically, those defined by formula (I) set forth above. The complex can be formed prior to introduction to the polymerization vessel, or components (reactants) can be added separately and permitted to react so as to form the complex, and therefore the catalyst, in situ.

In formula (I), M represents a Group 3 metal atom. Where M is a lanthanide series metal, it preferably is Nd or Gd. M can be in any of a number of oxidation states, with +2 to +5 being common and +3 being perhaps the most common.

Again referring to formula (I), L represents a neutral Lewis base, examples of which include but are not limited to cyclic or acyclic (thio)ethers, amines, and phosphines. Specific non-limiting examples of L groups include THF, diethyl ether, dimethyl aniline, trimethyl phosphine, neutral olefins, neutral diolefins, and the like. Use of ethers and cyclic ethers as L in formula (I) complexes can be preferred.

Again referring to formula (I), z can be an integer of from 0 to 3 (determined by the available coordination number(s) of M), so the complex can contain no L groups, one L group, or a plurality of L groups. In some embodiments, preference can be given to complexes where z is 0; examples of such embodiments are given below in the examples section. Where z is 2 or 3, each L can be the same or different, although preference can be given to those complexes where each L is the same.

Again referring to formula (I), each $R^2$ independently is an X-type, monoanionic ligand (of the CBC method, see Green, "A new approach to the formal classification of covalent compounds of the elements." *J. Organomet. Chem.*, 500 (1-2), pp. 127-48 (1995)). Non-limiting examples of $R^2$ include H; a halogen atom, especially Cl or Br; a silyl group; a siloxy group; a nitro group; a sulfonate group; an amido group; a silylalkyl group; an alkoxy, particularly a $C_1$-$C_6$ alkoxy, group; and a $C_1$-$C_{20}$, particularly a $C_1$-$C_{12}$, substituted or unsubstituted, straight-chain or branched (perfluoro) alkyl group (including, but not limited to, methyl, ethyl, n-propyl, isopropyl, n-butyl, isobutyl, sec-butyl, tert-butyl, neopentyl, n-hexyl, and octyl), aralkyl group, allyl group, amino group or substituted or unsubstituted aryl group (including, but not limited to, phenyl, tolyl, benzyl, naphthyl, biphenyl, phenanthryl, anthracenyl and terphenyl). Al- and B-containing groups represented, respectively, by $AlR^7_4$ and $BR^7_4$ where $R^7$ is H, a halogen atom, a substituted or unsubstituted aryl group, etc., also can serve as an $R^2$ group. Those embodiments where $R^2$ bonds to or associates with M via a C atom might permit the use of simpler catalysts systems, a point discussed in more detail below. Any of a variety of bis(silyl) amino groups constitute preferred $R^2$ groups in certain embodiments.

For substituted $R^2$ groups, exemplary substituents include, but are not limited to halogen atoms, halo-substituted groups (e.g., halogenated $C_1$-$C_{30}$, particularly $C_1$-$C_8$, hydrocarbyl groups such as trifluoromethyl, pentafluorophenyl, and chlorophenyl), other $C_1$-$C_{30}$, particularly $C_1$-$C_8$, hydrocarbyl groups (e.g., aryl-substituted alkyl groups such as benzyl and cumyl), heteroatom-containing groups (e.g., alkoxy, aryloxy such as 2,6-dimethylphenoxy or 2,4,6-trimethylphenoxy, acyl such as p-chlorobenzoyl or p-methoxybenzoyl, (thio)carboxyl, carbonato, hydroxy, peroxy, (thio) ester such as acetyloxy or benzoyloxy, (thio)ether, anhydride, amino, imino, amide such as acetamido or N-methylacetamido, imide such as acetimido and benzimido, hydrazino, hydrazono, nitro, nitroso, (iso)cyano, (thio)cyanic acid ester, amidino, diazo, borandiyl, borantriyl, diboranyl, mercapto, dithioester, alkylthio, arylthio such as (methyl)phenylthio or naphthylthio, thioacyl, isothiocyanic acid ester, sulfonester, sulfonamide, dithiocarboxyl, sulfo, sulfonyl, sulfinyl, sulfenyl, sulfonate, phosphido, (thio)phosphoryl, phosphato, silyl, siloxy, hydrocarbyl-substituted silyl groups such as methylsilyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl, dimethyl(pentafluorophenyl)silyl, bistrimethylsilylmethyl, and hydrocarbyl-substituted siloxy groups such as trimethylsiloxy), and the like. (Replacing the silicon atom in the Si-containing groups with Ge or Sn can provide useful Ge- or Sn-containing groups.)

Alternatively, one $R^2$ and one L, together with the M atom, can join to form a cyclic moiety, typically a 5- or 6-membered ring that optionally contains one or more heteroatoms in addition to the M atom. Optionally, the cyclic moiety can include one or more pendent substituents such as, but not limited to, substituted or unsubstituted aryl and $C_1$-$C_{20}$ (particularly $C_1$-$C_6$) alkyl groups.

Again referring to formula (I), each $R^1$ independently is H, a halogen atom, a $C_1$-$C_{20}$ (particularly $C_1$-$C_6$) alkyl group, a $C_5$-$C_8$ cycloalkyl group, an aralkyl group, an alkoxy group, a siloxy group, a nitro group, a sulfonate group, or a —$(CH_2)_y R^3$ group where y is 0 or 1 and where $R^3$ is a substituted or unsubstituted aryl group, preferably a phenyl group.

Where $R^3$ of a —$(CH_2)_y R^3$ group is an alkyl-substituted phenyl group, the position of the alkyl substituent can impact the properties of the resulting polymer, e.g., a methyl group at the 4-position of the phenyl ring can yield a polymer with more isolated polyene mer than an analogous complex with a methyl group at the 2-position. The term "isolated" relates to the numerical amount of polyene mer not adjacent to at least one other polyene mer, as evidenced by peak(s) at ~32.1 and/or ~32.2 ppm in a $^{13}C$ NMR spectroscopy plot and/or by peak(s) at between ~1.85 and ~2.02 ppm in a $^1H$ NMR spectroscopy plot. The percentage of such isolated polyene mer can be calculated by dividing the heights of the peaks at these shifts by the sum of the heights of all peaks due to polyene mer, e.g., all peaks between ~1.85 and ~2.20 ppm for $^1H$ NMR and peaks at ~27.3, 32.1, 32.2, and 32.4 ppm for $^{13}C$ NMR.

In certain embodiments, all $R^1$ groups can be selected from alkyl and —$(CH_2)_y R^3$ groups; in certain of these, as well as other embodiments, all $R^1$ groups can be the same.

Generally, formula (I)-type complexes where each $R^1$ is an alkyl group, regardless of whether each $R^1$ is the same is different, tend to yield polymers with the lowest levels of vinyl mer, i.e., diene mer having 1,2-microstructure.

Formula (I)-type complexes where at least one $R^1$ is a —$(CH_2)_y R^3$ group, particularly a substituted or unsubstituted benzyl group, have been found to be capable of producing polymers having unusual and very desirable properties. For example, while these types of complexes can provide olefin/ polyene interpolymers having a high amounts of polyene mer incorporated in a 1,4-configuration, those interpolymers can be random (i.e., few to no blocks of either olefin or polyene mer and having large amounts of isolated polyene mer) or can include a block of polyene mer along with at least one segment (a block or microblock) that has randomly distributed polyene and olefin mer; advantageously, the block interpolymer embodiments can be achieved without the need for staged addition of different monomers, although such staged addition is not excluded from the process of the present invention. Additionally or alternatively, these types of complexes can result in interpolymers having higher amounts of ethylene than can analogous complexes not including at least one —(CH$_2$)R$^3$ group as an R$^1$.

While the amount of isolated polyene mer typically is quite low, i.e., usually less than 10 mole percent, commonly less than ~5 mole percent and often less than 1 mole percent, formula (I)-type complexes where at least one R$^1$ is a —(CH$_2$)R$^3$ group can produce polymers where the amount of such "isolated" polyene mer is quite high i.e., typically more than 25 mole percent, commonly more than ~30 mole percent and often more than 40 mole percent; in certain embodiments, the amount of such "isolated" polyene mer can be above 75, 80 or even 85 mole percent. (All percentages in this paragraph are based on the total moles of polyene mer.)

Two R$^1$ groups, together with the Si atom to which each is bonded, optionally can join to form a cyclic moiety, typically a 5- or 6-membered ring that optionally contains one or more heteroatoms in addition to the M atom. Optionally, the cyclic moiety can include one or more pendent substituents such as, but not limited to, substituted or unsubstituted C$_1$-C$_6$ alkyl groups.

For R$^1$, R$^2$ and R$^3$, exemplary substituents include, but are not limited to halogen atoms, halo-substituted groups (e.g., halogenated C$_1$-C$_{30}$ hydrocarbyl groups such as trifluoromethyl, pentafluorophenyl, and chlorophenyl), other hydrocarbyl groups (e.g., aryl-substituted alkyl groups such as benzyl and cumyl), heteroatom-containing groups (e.g., alkoxy, aryloxy such as 2,6-dimethylphenoxy or 2,4,6-trimethylphenoxy, acyl such as p-chlorobenzoyl or p-methoxybenzoyl, (thio)carboxyl, carbonato, hydroxy, peroxy, (thio)ester such as acetyloxy or benzoyloxy, (thio)ether, anhydride, amino, imino, amide such as acetamido or N-methylacetamido, imide such as acetimido and benzimido, hydrazino, hydrazono, nitro, nitroso, cyano, isocyano, (thio)cyanic acid ester, amidino, diazo, borandiyl, borantriyl, diboranyl, mercapto, dithioester, alkylthio, arylthio such as (methyl)phenylthio, or naphthylthio, thioacyl, isothiocyanic acid ester, sulfonester, sulfonamide, dithiocarboxyl, sulfo, sulfonyl, sulfinyl, sulfenyl, phosphido, (thio) phosphoryl, phosphato, silyl, siloxy, hydrocarbyl-substituted silyl groups such as methylsilyl, dimethylsilyl, trimethylsilyl, ethylsilyl, diethylsilyl, triethylsilyl, diphenylmethylsilyl, triphenylsilyl, dimethylphenylsilyl, dimethyl-t-butylsilyl, dimethyl(pentafluorophenyl)silyl, bistrimethylsilylmethyl, and hydrocarbyl-substituted siloxy groups such as trimethylsiloxy), and the like. (Replacing the silicon atom in the Si-containing groups with Ge or Sn can provide useful Ge- or Sn-containing groups.) The Al- and B-containing groups can be represented, respectively, by AlR$^7_4$ and BR$^7_4$ where R$^7$ is H, a halogen atom, a substituted or unsubstituted aryl group, etc.

Again referring to formula (I), the variable n can be either 1 or 2, with the resulting complexes being represented below by, respectively, formulas (Ia) and (Ib):

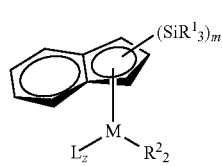

(Ia)

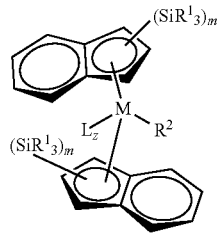

(Ib)

Depending on the value of z, M in the formula (Ia) complexes can be involved in from 3 to 6 bonds. The coordination numbers of Group 3 metal atoms, particularly lanthanide metal atoms, in organometallic complexes can range from 3 to 12, with the bulkiness of the ligands being the primary deciding factor on the upper limit. Such metal atoms typically have a coordination number of at least 6, but bulky ligands can result in lower coordination numbers. Therefore, particularly where R$^2$ is a relatively bulky ligand, z might be limited to 0 to 2 inclusive, or even 0 or 1.

The values of both n and z also can impact the identity of the R$^2$ group(s). For example, where n=2 and/or z≥1, a bis(trialkylsilyl) amino group as an R$^2$ group might be too bulky to permit the complex to be synthesized, at least efficiently or in high yields. Thus, one of the alkyl groups attached to the silyl Si atom might need to be replaced with a smaller group or atom, e.g., an H atom. (This is intended to be an exemplary teaching, which the ordinarily skilled artisan can use to guide selection of appropriate number and types of ligands.)

The variable m in formula (I)-type complexes is 1 or 2. When m=2, the —SiR$^1_3$ groups typically are located at the 1 and 3 positions of the indenyl ligand. Using the formula (Ia) complex above for exemplary purposes, this can be represented as follows:

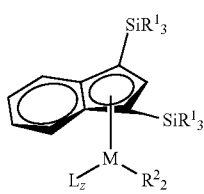

(Ia-1)

The ordinarily skilled artisan easily can extend this description to envision the substitutions on the general formula (Ib)-type bis-indenyl complexes.

Formula (I)-type complexes can be prepared by known procedures, examples of which are described in the examples section below, the teaching of which can be extended or modified readily by the ordinarily skilled artisan.

Component (b) of the catalyst composition, referred to herein as a co-catalyst or catalyst activator, includes an alkylating agent and/or a compound containing a non-coordinating anion or a non-coordinating anion precursor.

An alkylating agent can be considered to be an organometallic compound that can transfer hydrocarbyl groups to another metal. These agents typically are organometallic compounds of electropositive metals such as Groups 1, 2, and 13 metals. Exemplary alkylating agents include organoaluminum compounds such as those having the general formula $AlR^8_oX_{3-o}$ where o is an integer of from 1 to 3 inclusive; each $R^8$ independently is a monovalent organic group, which may contain heteroatoms such as N, O, B, Si, S, P, and the like, connected to the Al atom via a C atom; and each X independently is H, a halogen atom, a carboxylate group, an alkoxide group, or an aryloxide group. In one or more embodiments, each $R^8$ independently can be a hydrocarbyl group such as, for example, alkyl, cycloalkyl, substituted cycloalkyl, alkenyl, cycloalkenyl, substituted cycloalkenyl, aryl, substituted aryl, aralkyl, alkaryl, allyl, and alkynyl groups, with each group containing from a single C atom, or the appropriate minimum number of C atoms to form the group, up to about 20 C atoms. These hydrocarbyl groups may contain heteroatoms including, but not limited to, N, O, B, Si, S, and P atoms. Non-limiting species of organoaluminum compounds within this general formula include

- trihydrocarbylaluminum compounds such as trimethylaluminum, triethylaluminum, triisobutylaluminum (TIBA), tri-n-propylaluminum, triisopropylaluminum, tri-n-butylaluminum, tri-t-butylaluminum, tri-n-pentylaluminum, trineopentylaluminum, tri-n-hexylaluminum, tri-n-octylaluminum, tris(2-ethylhexyl)aluminum, tricyclohexylaluminum, tris(1-methylcyclopentyl)aluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum, and ethyldibenzylaluminum;
- dihydrocarbylaluminum hydrides such as diethylaluminum hydride, di-n-propylaluminum hydride, diisopropylaluminum hydride, di-n-butylaluminum hydride, diisobutylaluminum hydride (DIBAH), di-n-octylaluminum hydride, diphenylaluminum hydride, di-p-tolylaluminum hydride, dibenzylaluminum hydride, phenylethylaluminum hydride, phenyl-n-propylaluminum hydride, phenylisopropylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisopropylaluminum hydride, p-tolyl-n-butylaluminum hydride, p-tolylisobutylaluminum hydride, p-tolyl-n-octylaluminum hydride, benzylethylaluminum hydride, benzyl-n-propylaluminum hydride, benzylisopropylaluminum hydride, benzyl-n-butylaluminum hydride, benzylisobutylaluminum hydride, and benzyl-n-octylaluminum hydride;
- hydrocarbylaluminum dihydrides such as ethylaluminum dihydride, n-propylaluminum dihydride, isopropylaluminum dihydride, n-butylaluminum dihydride, isobutylaluminum dihydride, and n-octylaluminum dihydride;
- dihydrocarbylaluminum carboxylates;
- hydrocarbylaluminum bis(carboxylate)s;
- dihydrocarbylaluminum alkoxides;
- hydrocarbylaluminum dialkoxides;
- dihydrocarbylaluminum halides such as diethylaluminum chloride (DEAC), di-n-propylaluminum chloride, diisopropylaluminum chloride, di-n-butylaluminum chloride, diisobutylaluminum chloride, di-n-octylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenyl-n-butylaluminum chloride, phenylisobutylaluminum chloride, phenyl-n-octylaluminum chloride, p-tolylethylaluminum chloride, p-tolyl-n-propylaluminum chloride, p-tolylisopropylaluminum chloride, p-tolyl-n-butylaluminum chloride, p-tolylisobutylaluminum chloride, p-tolyl-n-octylaluminum chloride, benzylethylaluminum chloride, benzyl-n-propylaluminum chloride, benzylisopropylaluminum chloride, benzyl-n-butylaluminum chloride, benzylisobutylaluminum chloride, and benzyl-n-octylaluminum chloride;
- hydrocarbylaluminum dihalides such as ethylaluminum dichloride, n-propylaluminum dichloride, isopropylaluminum dichloride, n-butylaluminum dichloride, isobutylaluminum dichloride, and n-octylaluminum dichloride;
- dihydrocarbylaluminum aryloxides; and
- hydrocarbylaluminum diaryloxides.

In certain embodiments, the alkylating agent can include trihydrocarbylaluminum, dihydrocarbylaluminum hydride, and/or hydrocarbylaluminum dihydride.

Other organoaluminum compounds that can serve as alkylating agents include, but are not limited to, dimethylaluminum hexanoate, diethylaluminum octoate, diisobutylaluminum 2-ethylhexanoate, dimethylaluminum neodecanoate, diethylaluminum stearate, diisobutylaluminum oleate, methylaluminum bis(hexanoate), ethylaluminum bis(octoate), isobutylaluminum bis(2-ethylhexanoate), methylaluminum bis(neodecanoate), ethylaluminum bis(stearate), isobutylaluminum bis(oleate), dimethylaluminum methoxide, diethylaluminum methoxide, diisobutylaluminum methoxide, dimethylaluminum ethoxide, diethylaluminum ethoxide, diisobutylaluminum ethoxide, dimethylaluminum phenoxide, diethylaluminum phenoxide, diisobutylaluminum phenoxide, methylaluminum dimethoxide, ethylaluminum dimethoxide, isobutylaluminum dimethoxide, methylaluminum diethoxide, ethylaluminum diethoxide, isobutylaluminum diethoxide, methylaluminum diphenoxide, ethylaluminum diphenoxide, and isobutylaluminum diphenoxide.

Aluminoxanes constitute another class of organoaluminum compounds suitable for use as an alkylating agent. (These compounds also can serve as activators after the alkylating activity is complete.) This class includes oligomeric linear aluminoxanes and oligomeric cyclic aluminoxanes, formulas for both being provided in a variety of references including, for example, U.S. Pat. No. 8,017,695. (Where the oligomeric type of compound is used as an alkylating agent, the number of moles refers to the number of moles of Al atoms rather than the number of moles of oligomeric molecules, a convention commonly employed in the art of catalyst systems utilizing aluminoxanes.)

Aluminoxanes can be prepared by reacting trihydrocarbylaluminum compounds with water. This reaction can be performed according to known methods such as, for example, (1) dissolving the trihydrocarbylaluminum compound in an organic solvent and then contacting it with water, (2) reacting the trihydrocarbylaluminum compound with water of crystallization contained in, for example, metal salts, or water adsorbed in inorganic or organic compounds, or (3) reacting the trihydrocarbylaluminum compound with water in the presence of the monomer(s) to be polymerized.

Suitable aluminoxane compounds include, but are not limited to, methylaluminoxane (MAO), modified methylaluminoxane (MMAO, formed by substituting ~20 to 80% of the methyl groups of MAO with $C_2$-$C_{12}$ hydrocarbyl groups, preferably with isobutyl groups, using known techniques), ethylaluminoxane, n-propylaluminoxane, isopropylaluminoxane, butylaluminoxane, isobutylaluminoxane, n-pentylaluminoxane, neopentylaluminoxane, n-hexylaluminoxane, n-octylaluminoxane, 2-ethylhexylaluminoxane, cyclohexylaluminoxane, 1-methylcyclopentylaluminoxane, phenylaluminoxane, and 2,6-dimethylphenylaluminoxane.

Aluminoxanes can be used alone or in combination with other organoaluminum compounds. In one embodiment, MAO and at least one other organoaluminum compound such as DIBAH can be employed in combination. The interested reader is directed to U.S. Pat. No. 8,017,695 for other examples of aluminoxanes and organoaluminum compounds employed in combination.

Also suitable as alkylating agents are organozinc (particularly dialkyl zinc) compounds as well as organomagnesium compounds such as those having the general formula $R^9_g MgX_{2-g}$ where X is defined as above, g is 1 or 2, and $R^9$ is the same as $R^8$ except that each monovalent organic group is connected to the Mg atom via a C atom. Potentially useful organomagnesium compounds include, but are not limited to, diethylmagnesium, di-n-propylmagnesium, diisopropylmagnesium, dibutylmagnesium, dihexylmagnesium, diphenylmagnesium, dibenzylmagnesium, hydrocarbylmagnesium hydride (e.g., methylmagnesium hydride, ethylmagnesium hydride, butylmagnesium hydride, hexylmagnesium hydride, phenylmagnesium hydride, and benzylmagnesium hydride), hydrocarbylmagnesium halide (e.g., methylmagnesium chloride, ethylmagnesium chloride, butylmagnesium chloride, hexylmagnesium chloride, phenylmagnesium chloride, benzylmagnesium chloride, methylmagnesium bromide, ethylmagnesium bromide, butylmagnesium bromide, hexylmagnesium bromide, phenylmagnesium bromide, and benzylmagnesium bromide), hydrocarbylmagnesium carboxylate (e.g., methylmagnesium hexanoate, ethylmagnesium hexanoate, butylmagnesium hexanoate, hexylmagnesium hexanoate, phenylmagnesium hexanoate, and benzylmagnesium hexanoate), hydrocarbylmagnesium alkoxide (e.g., methylmagnesium ethoxide, ethylmagnesium ethoxide, butylmagnesium ethoxide, hexylmagnesium ethoxide, phenylmagnesium ethoxide, and benzylmagnesium ethoxide), and hydrocarbylmagnesium aryloxide (e.g., methylmagnesium phenoxide, ethylmagnesium phenoxide, butylmagnesium phenoxide, hexylmagnesium phenoxide, phenylmagnesium phenoxide, and benzylmagnesium phenoxide).

Many species of a formula (I) complex having an $R^2$ group which bonds to or associates with M via a C atom can be used in a catalyst composition without an alkylating agent.

The catalyst composition also or alternatively can contain a non-coordinating anion or a non-coordinating anion precursor. Exemplary non-coordinating anions include borate anions, particularly fluorinated tetraarylborate anions. Specific examples of non-coordinating anions include tetraphenylborate, tetrakis(monofluorophenyl) borate, tetrakis(difluorophenyl) borate, tetrakis(trifluororphenyl) borate, tetrakis(tetrafluorophenyl) borate, tetrakis(pentafluorophenyl) borate, tetrakis(tetrafluoromethylphenyl) borate, tetra (tolyl) borate, tetra(xylyl) borate, [tris(phenyl), pentafluorophenyl] borate, [tris(pentafluorophenyl), phenyl] borate, tridecahydride-7,8-dicarbaundecaborate and the like. Tetrakis(pentafluorophenyl) borate is among the preferred non-coordinating anions.

Compounds containing a non-coordinating anion also contain a countercation such as a carbonium (e.g., trisubstituted carbonium cation such as triphenylcarbonium cation, tri(substituted phenyl)carbonium cation (e.g., tri(methylphenyl)carbonium cation), oxonium, ammonium (e.g., trialkyl ammonium cations, N,N-dialkyl anilinium cations, dialkyl ammonium cations, etc.), phosphonium (e.g., triaryl phosphonium cations such as triphenyl phosphonium cation, tri(methylphenyl)phosphonium cation, tri(dimethylphenyl) phosphonium cation, etc.), cycloheptatrieneyl, or ferrocenium cation (or similar). Among these, N,N-dialkyl anilinium or carbonium cations are preferred, with the former being particularly preferred.

Examples of compounds containing a non-coordinating anion and a counter cation include triphenylcarbonium tetrakis(pentafluorophenyl)borate, N,N-dimethylanilinium tetrakis(pentafluorophenyl)borate, triphenylcarbonium tetrakis[3,5-bis(trifluoromethyl)phenyl]borate, and N,N-dimethylanilinium tetrakis[3,5-bis(trifluoromethyl)phenyl] borate.

Exemplary non-coordinating anion precursors include boron compounds that include strong electron-withdrawing groups. Specific examples include triarylboron compounds where each aryl group is strongly electron withdrawing, e.g., pentafluorophenyl or 3,5-bis(trifluoromethyl)phenyl.

Certain species of a formula (I) complex having an $R^2$ group which bonds to or associates with M via a C atom can be used in a catalyst composition without a non-coordinating anion or a non-coordinating anion precursor.

Catalyst compositions of the type just described have very high catalytic activity for polymerizing polyenes such as conjugated dienes (and optionally olefins, particularly α-olefins including ethylene) into stereospecific polymers over a wide range of concentrations and ratios, although polymers having the most desirable properties typically are obtained from systems that employ a relatively narrow range of concentrations and ratios of ingredients. Further, the catalyst composition ingredients are believed to interact to form an active catalyst species, so the optimum concentration for each ingredient can depend on the concentrations of the other ingredients. The following molar ratios are considered to be relatively exemplary for a variety of different systems based on the foregoing ingredients:

alkylating agent to formula (I) complex: from ~1:1 to ~1000:1, commonly from ~2:1 to ~500:1, typically from ~5:1 to ~200:1;

aluminoxane to formula (I) complex, specifically equivalents of aluminum atoms in the aluminoxane to equivalents of Group 3 atoms in the complex: from ~5:1 to ~1000:1, commonly from ~10:1 to ~700:1, typically from ~20:1 to ~500:1;

organoaluminum compound to formula (I) complex: from ~1:1 to ~200:1, commonly from ~2:1 to ~150:1, typically from ~5:1 to ~100:1; and non-coordinating anion or precursor to formula (I) complex: from ~1:2 to ~20:1, commonly from ~3:4 to ~10:1, typically from ~1:1 to ~6:1.

The molecular weight of polymers produced with a formula (I) complex-containing catalyst composition can be impacted by adjusting the amount of metallic complex used and/or the amounts of co-catalyst compound concentrations within the catalyst composition; polymers having a wide range of molecular weights can be produced in this manner. In general, increasing the metallic complex and co-catalyst concentrations reduces the molecular weight of resulting polymers, although very low molecular weight polymers (e.g., liquid polydienes) require extremely high catalyst concentrations. Typically, this necessitates removal of catalyst residues from the polymer to avoid adverse effects such as retardation of the sulfur cure rate.

A formula (I) complex-containing catalyst composition can be formed using any of the following methods:

(1) In situ. The catalyst ingredients are added to a solution containing monomer and solvent (or simply bulk monomer). The addition can occur in a stepwise or simultaneous manner. In the case of the latter, the alkylating agent preferably is added first followed by the formula (I) complex.

(2) Pre-mixed. The ingredients can be mixed outside the polymerization system, generally at a temperature of from about −20° to ~80° C., before being introduced to the monomer(s).

(3) Pre-formed in the presence of monomer(s). The catalyst ingredients are mixed in the presence of a small amount of monomer(s) at a temperature of from about −20° to ~80° C. The amount of monomer(s) can range from ~1 to ~500 moles, commonly from ~5 to ~250 moles, typically from ~10 to ~100 moles, per mole of the formula (I) complex. The resulting catalyst composition is added to the remainder of the monomer(s) to be polymerized.

(4) Two-stage procedure.
(a) The alkylating agent is combined with the formula (I) complex in the absence of monomer or in the presence of a small amount of monomer(s) at a temperature of from about −20° to ~80° C.
(b) The foregoing mixture and the remaining components are charged in either a stepwise or simultaneous manner to the remainder of the monomer(s) to be polymerized.

When a solution of one or more of the catalyst ingredients is prepared outside the polymerization system in the foregoing methods, an organic solvent or carrier preferably is employed; useful organic solvents include those mentioned previously. In other embodiments, one or more monomers can be used as a carrier or the catalyst ingredients can be employed neat, i.e., free of any solvent of other carrier.

In one or more embodiments, some or all of the catalyst composition can be supported on an inert carrier. The support can be a porous solid such as talc, a sheet silicate, an inorganic oxide or a finely divided polymer powder. Suitable inorganic oxides are oxides of elements from any of Groups 2-5 and 13-16. Exemplary supports include $SiO_2$, aluminum oxide, and also mixed oxides of the elements Ca, Al, Si, Mg or Ti and also corresponding oxide mixtures, Mg halides, styrene/divinylbenzene copolymers, polyethylene or polypropylene.

Ordinarily skilled artisans recognize that varying the amounts of the components of a catalyst composition (as well as the solvent system) can greatly affect both the efficiency of the catalyst system as well as the composition and microstructure of the resulting polymer. For example, for catalyst compositions that include an alkylating agent as component (b), increasing the relative concentration of the alkylating agent might result in polymers with lower molecular weights (regardless of whether measured as $M_n$, $M_w$, or $M_p$) and/or less isolated polyene units, although the latter characteristic might be at least somewhat dependent on the composition of the solvent system (e.g., the effect might be more evident in an aromatic solvent like toluene).

Similarly, the amount of time that the catalyst composition is permitted to contact the monomers can affect the size, mer composition and, to a lesser extent, microstructure of the resulting polymer.

Further, the nature of the solvent system can affect both the process and the resulting polymer. For example, solvent systems made from one or more alkanes often require higher concentrations of the catalyst composition than do solvent systems consisting of other organic liquid(s). However, polymerization processes conducted in such solvent systems can yield interpolymers with higher amounts of olefin mer than can an essentially identical process conducted in another type of solvent system, perhaps due to increased solubility of olefin monomer in an alkane-based solvent system.

Choice of M, m, n, z, $R^1$ and $R^2$ likewise can have major impacts on process and product characteristics. As a non-limiting example, formula (I)-type complexes where M is Gd and particularly Nd often yield interpolymers having higher levels of isolated polyene mer.

The production of polymers such as polydienes (or interpolymers that include diene mer) is accomplished by polymerizing conjugated diene monomer(s) in the presence of a catalytically effective amount of a catalyst composition as described above. The total catalyst concentration to be employed in the polymerization mass depends on the interplay of multiple factors such as the purity of ingredients, the polymerization temperature, the polymerization rate and conversion desired, and the molecular weight desired. Accordingly, a specific total catalyst concentration cannot be definitively set forth except to say that catalytically effective amounts of the respective catalyst ingredients should be used. The amount of the formula (I) complex used generally ranges from ~0.005 to ~2 mmol, commonly from ~0.01 to ~1 mmol, typically from ~0.02 to ~0.5 mmol per 100 g monomer. All other ingredients generally can be added in amounts based on the amount of formula (I) complex; see the various ratios set forth above.

Where an olefin interpolymer is desired, the molar ratio of polyene (e.g., conjugated diene) to olefin introduced into the reaction vessel can vary over a wide range. For example, the molar ratio of polyene (e.g., conjugated diene) to olefin can range from ~100:1 to 1:100, commonly from ~20:1 to 1:20, and typically from ~5:1 to 1:5.

Polymerization preferably is carried out in one or more organic solvents of the type(s) set forth above, i.e., as a solution polymerization (where both the monomer(s) and the polymers formed are soluble in the solvent) or precipitation polymerization (where the monomer is in a condensed phase but the polymer products are insoluble). The catalyst ingredients preferably are solubilized or suspended in the organic liquid, and additional solvent (beyond that used in preparing the catalyst composition) usually is added to the polymerization system; the additional solvent(s) may be the same as or different from the solvent(s) used in preparing the catalyst composition. In one or more embodiments, the solvent content of the polymerization mixture may be more than 20%, more than 50%, or even more than 80% (by wt.) of the total weight of the polymerization mixture. The concentration of monomer present at the beginning of the polymerization generally ranges from ~3 to ~80%, commonly from ~5 to ~50%, and typically from ~10% to ~30% (by wt.).

In certain embodiments, a bulk polymerization system that includes no more than a minimal amount of solvent can be used, i.e., a bulk polymerization process where one or more of the monomers act(s) as the solvent; examples of potentially useful bulk polymerization processes are disclosed in U.S. Pat. No. 7,351,776. In a bulk polymerization, the solvent content of the polymerization mixture may be less than ~20%, less than ~10%, or even less than ~5% (by wt.) of the total weight of the polymerization mixture. The polymerization mixture even can be substantially devoid of solvent, i.e., contain less than that amount of solvent which otherwise would have an appreciable impact on the polymerization process.

The polymerization can be conducted in any of a variety of reaction vessels. For example, solution polymerizations can be conducted in a conventional stirred-tank reactor. Bulk polymerizations also can be conducted in a stirred-tank reaction if the monomer conversion is less than ~60%. Where monomer conversion is higher than ~60%, which typically results in a highly viscous polymer cement (i.e., mixture of solvent, polymers and any remaining monomer(s)), bulk polymerization can be conducted in an elongated reactor in which the viscous cement is driven by, for example, piston or self-cleaning single- or double-screw agitator.

All components used in or during the polymerization can be combined in a single vessel (e.g., a stirred-tank reactor), and the entirety of the polymerization process can be conducted in that vessel. Alternatively, two or more of the ingredients can be combined outside the polymerization vessel and transferred to another vessel where polymerization of the monomer(s), or at least a major portion thereof, can be conducted.

Surprisingly, polymerizations performed in solvent systems that include at least 50% (by wt.) of one or more $C_5$-$C_{10}$ alkanes (more expansively described above) can result in polyene/ethylene interpolymers having at least 10 mole percent, 20 mole percent, 25 mole percent, 33 mole percent, 40 mole percent or even 50 mole percent ethylene mer. These high amounts of ethylene mer contents are believed to have been previously unattainable in alkane-rich (or alkane-only) solvent systems.

Catalyst systems employing formula (I)-type complexes can result in polymers having previously unattainable mer content distributions and/or microstructures, certain of which are described in the following paragraphs (in which 1,3-butadiene is used as an exemplary polyene and ethylene as an exemplary but preferred α-olefin).

Catalyst compositions employing certain embodiments of the indenyl-metal complex can yield copolymers with randomly distributed butadiene and ethylene mer, but at least 40%, preferably at least 45% and more preferably at least 50% of the butadiene mer are present in a cis isomeric configuration. Catalyst compositions employing certain other embodiments of the indenyl-metal complex can yield copolymers with both a block of high cis butadiene mer (i.e., a block having the type of high cis isomeric configuration described in the preceding sentence) and a block of randomly distributed butadiene and ethylene mer.

The polymerization can be carried out as a batch, continuous, or semi-continuous process. The conditions under which the polymerization proceeds can be controlled to maintain the temperature of the polymerization mixture in a range of from −10° to ~200° C., commonly from ~0° to ~150° C., and typically from ~20° to ~100° C. Heat generated by the polymerization can be removed by external cooling by a thermally controlled reactor jacket and/or internal cooling (by evaporation and condensation of the monomer through use of a reflux condenser connected to the reactor). Also, conditions may be controlled to conduct the polymerization under a pressure of from ~0.01 to ~5 MPa, commonly from ~0.05 to ~3 MPa, typically from ~0.1 to ~2 MPa; the pressure at which the polymerization is carried out can be such that the majority of monomers are in the liquid phase. In these or other embodiments, the polymerization mixture may be maintained under anaerobic conditions, typically provided by an inert protective gas such as $N_2$, Ar or He.

Regardless of whether a batch, continuous, or semi-continuous process is employed, the polymerization preferably is conducted with moderate to vigorous agitation.

The described polymerization process advantageously results in polymer chains that possess reactive (pseudo-living) terminals, which can be further reacted with one or more functionalizing agents so as to provide a polymer with a terminal functionality. These types of polymers can be referred to as functionalized and are distinct from a propagating chain that has not been similarly reacted. In one or more embodiments, reaction between the functionalizing agent and the reactive polymer can proceed via an addition or substitution reaction.

The terminal functionality can be reactive or interactive with other polymer chains (propagating and/or non-propagating) or with other materials in a rubber compound such as particulate reinforcing fillers (e.g., carbon black). As described above, enhanced interactivity between a polymer and particulate fillers in rubber compounds improves the mechanical and dynamic properties of resulting vulcanizates. For example, certain functionalizing agents can impart a terminal functionality that includes a heteroatom to the polymer chain; such a functionalized polymer can be used in rubber compounds from which vulcanizates can be provided, and that vulcanizates can possess high temperature (e.g., 50° C.) hysteresis losses (as indicated by a reduction in high temperature tan δ values) that are less than those possessed by vulcanizates prepared from similar rubber compounds that do not include such functionalized polymers. Reductions in high temperature hysteresis loss can be at least 5%, at least 10%, or even at least 15%.

The functionalizing agent(s) can be introduced after a desired monomer conversion is achieved but prior to introduction of a quenching agent (a compound with a protic H atom) or after the polymerization mixture has been partially quenched. The functionalizing agent can be added to the polymerization mixture after a monomer conversion of at least 5%, at least 10%, at least 20%, at least 50%, or at least 80%. In certain embodiments, the functionalizing agent is added after complete, or substantially complete, monomer conversion. In particular embodiments, a functionalizing agent may be introduced to the polymerization mixture immediately prior to, together with, or after the introduction of a Lewis base as disclosed in U.S. Pat. No. 8,324,329.

Useful functionalizing agents include compounds that, upon reaction, provide a functional group at the end of a polymer chain without joining two or more polymer chains together, as well as compounds that can couple or join two or more polymer chains together via a functional linkage to form a single macromolecule. The ordinarily skilled artisan is familiar with numerous examples of terminal functionalities that can be provided through this type of post-polymerization functionalization with terminating reagents, coupling agents and/or linking agents. For additional details, the interested reader is directed to any of U.S. Pat. Nos. 4,015,061, 4,616,069, 4,906,706, 4,935,471, 4,990,573, 5,064,910, 5,153,159, 5,149,457, 5,196,138, 5,329,005, 5,496,940, 5,502,131, 5,567,815, 5,610,227, 5,663,398, 5,567,784, 5,786,441, 5,844,050, 6,812,295, 6,838,526, 6,992,147, 7,153,919, 7,294,680, 7,642,322, 7,671,136, 7,671,138, 7,732,534, 7,750,087, 7,816,483, 7,879,952, 8,063,153, 8,088,868, 8,183,324, 8,642,706, etc., as well as references cited in these patents and later publications citing these patents. Specific exemplary functionalizing compounds include metal halides (e.g., $SnCl_4$), $R^{10}{}_3SnCl$, $R^{10}{}_2SnCl_2$, $R^{10}SnCl_3$, metalloid halides (e.g., $SiCl_4$), carbodiimides, ketones, aldehydes, esters, quinones, N-cyclic amides, N,N'- disubstituted cyclic ureas, cyclic amides, cyclic ureas, Schiff bases, iso(thio)cyanates, metal ester-carboxylate complexes (e.g., dioxyltin bis(octylmaleate), 4,4'-bis(diethylamino) benzophenone, alkyl thiothiazolines, alkoxysilanes (e.g., $Si(OR^{10})_4$, $R^{10}Si(OR^{10})_3$, $R^{10}{}_2Si(OR^{10})_2$, etc.), cyclic siloxanes, alkoxystannanes, and mixtures thereof. (In the foregoing, each $R^{10}$ independently is a $C_1$-$C_{20}$ alkyl group, $C_3$-$C_{20}$ cycloalkyl group, $C_6$-$C_{20}$ aryl group, or $C_7$-$C_{20}$ aralkyl group.) Commonly used exemplary functionalizing compounds include $SnCl_4$, tributyl tin chloride, dibutyl tin dichloride, and 1,3-dimethyl-2-imidazolidinone (DMI).

The amount of functionalizing agent added to the polymerization mixture can depend on various factors including the amount of formula (I) complex used, the type of functionalizing agent, the desired level of functionality, etc. In one or more embodiments, the amount of functionalizing agent may be in a range of from ~1 to ~200 moles, commonly from ~5 to ~150 moles, and typically from ~10 to ~100 moles per mole of formula (I) complex.

Because reactive polymer chains slowly self-terminate at high temperatures, the functionalizing agent can be added to the polymerization mixture when or soon after a peak polymerization temperature is observed or, at least in some embodiments, within 30±10 minutes thereafter. Reaction of these types of compounds with a terminally active polymer can be performed relatively quickly (a few minutes to a few hours) at moderate temperatures (e.g., 0° to 75° C.).

The functionalizing agent can be introduced to the polymerization mixture at a location (e.g., within a vessel) where the polymerization, or at least a portion thereof, has been conducted or at a location distinct therefrom. For example, the functionalizing agent can be introduced to the polymerization mixture in downstream vessels including downstream reactors or tanks, in-line reactors or mixers, extruders, or devolatilizers.

Although not mandatory, if desired, quenching can be performed to inactivate any residual reactive copolymer chains and the catalyst composition. Quenching can be conducted by stirring the polymer and an active hydrogen-containing compound, such as an alcohol or acid, for up to ~120 minutes at temperatures of from 25° to ~150° C. In some embodiments, the quenching agent can include a polyhydroxy compound as disclosed in U.S. Pat. No. 7,879, 958. An antioxidant such as 2,6-di-t-butyl-4-methylphenol (BHT) may be added along with, before, or after the addition of the quenching agent; the amount of antioxidant employed can be from ~0.2 to 1% (by wt.) of the polymer product. The quenching agent and the antioxidant can be added neat or, if necessary, dissolved in a hydrocarbon solvent or liquid monomer prior to being added to the polymerization mixture.

Once polymerization, functionalization (if any) and quenching (if any) are complete, the various constituents of the polymerization mixture can be recovered. Unreacted monomers can be recovered from the polymerization mixture by, for example, distillation or use of a devolatilizer. Recovered monomers can be purified, stored, and/or recycled back to the polymerization process.

The polymer product can be recovered from the polymerization mixture using known techniques. For example, the polymerization mixture can be passed through a heated screw apparatus, such as a desolventizing extruder, in which volatile substances (e.g., low boiling solvents and unreacted monomers) are removed by evaporation at appropriate temperatures (e.g., ~100° to ~170° C.) and under atmospheric or sub-atmospheric pressure. Another option involves steam desolvation followed by drying the resulting polymer crumbs in a hot air tunnel. Yet another option involves recovering the polymer directly by drying the polymerization mixture on a drum dryer. Any of the foregoing can be combined with coagulation with water, alcohol or steam; if coagulation is performed, oven drying may be desirable.

Recovered polymer can be grafted with other monomers and/or blended with other polymers (e.g., polyolefins) and additives to form resin compositions useful for various applications. The polymer, regardless of whether further reacted, is particularly suitable for use in the manufacture of various tire components including, but not limited to, tire treads, sidewalls, subtreads, and bead fillers. It also can be used as a compatibilizer for elastomeric blends and/or used in the manufacture of hoses, belts, shoe soles, window seals, other seals, vibration damping rubber, and other industrial or consumer products.

When the resulting polymer is utilized in a tread stock compound, it can be used alone or blended with any conventionally employed tread stock rubber including natural rubber and/or non-functionalized synthetic rubbers such as, e.g., one or more of homo- and interpolymers that include just polyene-derived mer units (e.g., poly(butadiene), poly (isoprene), and copolymers incorporating butadiene, isoprene, and the like), SBR, butyl rubber, neoprene, EPR, EPDM, acrylonitrile/butadiene rubber (NBR), silicone rubber, fluoroelastomers, ethylene/acrylic rubber, EVA, epichlorohydrin rubbers, chlorinated polyethylene rubbers, chlorosulfonated polyethylene rubbers, hydrogenated nitrile rubber, tetrafluoroethylene/propylene rubber and the like. When a functionalized polymer(s) is blended with conventional rubber(s), the amounts can vary from ~5 to ~99% of the total rubber, with the conventional rubber(s) making up the balance of the total rubber.

When the resulting polymer is utilized in a tread stock compound, it can be used alone or blended with any conventionally employed tread stock rubber including natural rubber and/or non-functionalized synthetic rubbers such as, e.g., one or more of homo- and interpolymers that include just polyene-derived mer units (e.g., poly(butadiene), poly (isoprene), and copolymers incorporating butadiene, isoprene, and the like), SBR, butyl rubber, neoprene, EPR, EPDM, acrylonitrile/butadiene rubber (NBR), silicone rubber, fluoroelastomers, ethylene/acrylic rubber, EVA, epichlorohydrin rubbers, chlorinated polyethylene rubbers, chlorosulfonated polyethylene rubbers, hydrogenated nitrile rubber, tetrafluoroethylene/propylene rubber and the like. When a functionalized polymer(s) is blended with conventional rubber(s), the amounts can vary from ~5 to ~99% of the total rubber, with the conventional rubber(s) making up the balance of the total rubber.

Amorphous silica ($SiO_2$) can be utilized as a filler. Silicas are generally classified as wet-process, hydrated silicas because they are produced by a chemical reaction in water, from which they are precipitated as ultrafine, spherical particles. These primary particles strongly associate into aggregates, which in turn combine less strongly into agglomerates. "Highly dispersible silica" is any silica having a very substantial ability to de-agglomerate and to disperse in an elastomeric matrix, which can be observed by thin section microscopy.

Surface area gives a reliable measure of the reinforcing character of different silicas; the Brunauer, Emmet and Teller ("BET") method (described in *J. Am. Chem. Soc.*, vol. 60, p. 309 et seq.) is a recognized method for determining surface area. BET surface area of silicas generally is less than 450 m²/g, and useful ranges of surface include from ~32 to ~400 m²/g, ~100 to ~250 m²/g, and ~150 to ~220 m²/g.

The pH of the silica filler is generally from ~5 to ~7 or slightly over, preferably from ~5.5 to ~6.8.

Some commercially available silicas which may be used include Hi-Sil™ 215, Hi-Sil™ 233, and Hi-Sil™ 190 (PPG Industries, Inc.; Pittsburgh, Pa.). Other suppliers of commercially available silica include Grace Engineered Materials (Baltimore, Md.), Evonik Industries (Parsippany, N.J.), Solvay (Cranbury, N.J.), and J.M. Huber Corp. (Edison, N.J.).

Silica can be employed in the amount of 1 to 100 phr, commonly in an amount from ~5 to ~80 phr. The useful upper range is limited by the high viscosity that such fillers can impart.

Other useful fillers include all forms of carbon black including, but not limited to, furnace black, channel blacks and lamp blacks. More specifically, examples of the carbon blacks include super abrasion furnace blacks, high abrasion furnace blacks, fast extrusion furnace blacks, fine furnace blacks, intermediate super abrasion furnace blacks, semi-reinforcing furnace blacks, medium processing channel blacks, hard processing channel blacks, conducting channel blacks, and acetylene blacks; mixtures of two or more of these can be used. Carbon blacks having a surface area (EMSA) of at least 20 m²/g, preferably at least ~35 m²/g, are preferred; surface area values can be determined by ASTM D-1765 using the CTAB technique. The carbon blacks may be in pelletized form or an unpelletized flocculent mass, although unpelletized carbon black can be preferred for use in certain mixers.

The amount of carbon black can be up to ~50 phr, with 5 to 40 phr being typical. When carbon black is used with silica, the amount of silica can be decreased to as low as ~1 phr; as the amount of silica decreases, lesser amounts of the processing aids, plus silane if any, can be employed.

Elastomeric compounds typically are filled to a volume fraction, which is the total volume of filler(s) added divided by the total volume of the elastomeric stock, of ~25%; accordingly, typical (combined) amounts of reinforcing fillers, i.e., silica and carbon black, is ~30 to 100 phr.

When silica is employed as a reinforcing filler, addition of a coupling agent such as a silane is customary so as to ensure good mixing in, and interaction with, the elastomer(s). Generally, the amount of silane that is added ranges between ~4 and 20%, based on the weight of silica filler present in the elastomeric compound.

Coupling agents generally include a functional group capable of bonding physically and/or chemically with a group on the surface of the silica filler (e.g., surface silanol groups) and a functional group capable of bonding with the elastomer, e.g., via a sulfur-containing linkage. Such coupling agents include organosilanes, in particular polysulfurized alkoxysilanes (see, e.g., U.S. Pat. Nos. 3,873,489, 3,978,103, 3,997,581, 4,002,594, 5,580,919, 5,583,245, 5,663,396, 5,684,171, 5,684,172, 5,696,197, etc.) or polyorganosiloxanes. An exemplary coupling agent is bis[3-(triethoxysilyl)propyl]tetrasulfide.

Addition of a processing aid can be used to reduce the amount of silane employed. See, e.g., U.S. Pat. No. 6,525,118 for a description of fatty acid esters of sugars used as processing aids. Additional fillers useful as processing aids include, but are not limited to, mineral fillers, such as clay (hydrous aluminum silicate), talc (hydrous magnesium silicate), and mica as well as non-mineral fillers such as urea and sodium sulfate. Preferred micas contain principally alumina, silica and potash, although other variants also can be useful. The additional fillers can be utilized in an amount of up to ~40 phr, typically up to ~20 phr.

Other conventional rubber additives also can be added. These include, for example, process oils, plasticizers, anti-degradants such as antioxidants and antiozonants, curing agents and the like.

All of the ingredients can be mixed using standard equipment such as, e.g., Banbury or Brabender mixers. Typically, mixing occurs in two or more stages. During the first stage (often referred to as the masterbatch stage), mixing typically is begun at temperatures of 120° to 130° C. and increases until a so-called drop temperature, typically 163°±3° C., is reached.

Where a formulation includes silica, a separate re-mill stage often is employed for separate addition of the silane component(s). This stage often is performed at temperatures similar to, although often slightly lower than, those employed in the masterbatch stage, i.e., ramping from ~90° C. to a drop temperature of ~150° C.

Reinforced rubber compounds conventionally are cured with ~0.2 to ~5 phr of one or more known vulcanizing agents such as, for example, sulfur or peroxide-based curing systems. For a general disclosure of suitable vulcanizing agents, the interested reader is directed to an overview such as that provided in Kirk-Othmer, *Encyclopedia of Chem. Tech.*, 3d ed., (Wiley Interscience, New York, 1982), vol. 20, pp. 365-468. Vulcanizing agents, accelerators, etc., are added at a final mixing stage. To ensure that onset of vulcanization does not occur prematurely, this mixing step often is done at lower temperatures, e.g., starting at ~60° to ~65° C. and not going higher than ~105° to ~110° C.

The following non-limiting, illustrative examples provide the reader with detailed conditions and materials that can be useful in the practice of the present invention.

EXAMPLES

Indene, chlorotrimethylsilane, tert-butyldimethylsilyl chloride, tribenzylsilyl chloride, benzyldimethylsilyl chloride and n-butyllithium were purchased from Sigma-Aldrich (St. Louis, Mo.), N,N-dimethylanilinium tetra(pentafluorophenyl)borate from Albemarle Corp. (Baton Rouge, La.), and trityltetra(pentafluorophenyl)borate from Strem Chemicals, Inc. (Newburyport, Mass.).

Literature methods were used to prepare the following compounds:
  1-tert-butyldimethylsilylindene, 1,3-bis(trimethylsilyl)indene and 1,3-bis(tert-butyldimethylsilyl)indene: A. Davison et al., *J. Organomet. Chem.*, 23(2), pp. 407-26 (1970) and C. A. Bradley et al., *Organometallics*, 23, pp. 5332-46 (2004),
  gadolinium(III) tris[N,N-bis(trimethylsilyl)amide]: D. C. Bradley et al., *J. Chem. Soc., Chem. Commun.*, pp. 349-50 (1972), and
  di(octadecyl)methylammonium tetrakis(pentafluorophenyl)borate: U.S. Pat. No. 5,919,983 (Rosen et al.).

In the chemical structures that follow, "Me" represents a methyl group.

Example 1a: 1-tribenzylsilylindene

To an oven-dried 500 mL Schlenk flask cooled under a stream of Ar was added 200 mL dry THF followed by 1.64 g (14.1 mmol) indene. This solution was cooled to −78° C. before dropwise addition over ~5 minutes of 9.29 mL of a 1.55 M solution of n-butyllithium in hexanes. The contents were stirred at this temperature for ~10 minutes.

The flask was transferred to an ice bath, and the contents were stirred for another ~30 minutes before 5.0 g (14.8 mmol) tribenzylsilyl chloride was added in one portion. After removal of the ice bath, the flask contents were allowed to warm to room temperature before being stirred for an additional ~16 hours.

Volatiles were removed, re-dissolved into hexanes and washed with 20 mL of a saturated $Na_2CO_3$ solution. The organic layer was separated, dried over $MgSO_4$ and concentrated on a rotary evaporator. The residue was subsequently purified under reduced pressure (~13.3 Pa, 0.1 torr) first to remove unreacted indene and then to isolate the desired product, 1-tribenzylsilylindene (4.3 g, ~40% yield).

Example 1b: 1-benzyldimethylsilylindene

To an oven-dried 500 mL Schlenk flask cooled under a stream of Ar was added 200 mL dry THF followed by 3.0 g (25.8 mmol) indene. This solution was cooled to −78° C. before dropwise addition over ~5 minutes of 16.9 mL of a 1.55 M solution of n-butyllithium in hexanes. The contents were stirred at this temperature for ~10 minutes.

The flask was transferred to an ice bath, and the contents were stirred for another ~30 minutes before 5.0 g (27.2 mmol) benzyldimethylsilyl chloride was added in one portion. After removal of the ice bath, the flask contents were allowed to warm to room temperature before being stirred for an additional ~16 hours.

Volatiles were removed, re-dissolved into hexanes and washed with 20 mL of a saturated $Na_2CO_3$ solution. The organic layer was separated, dried over $MgSO_4$ and concentrated on a rotary evaporator. The residue was subsequently purified under reduced pressure (~13.3 Pa, 0.1 torr) first to remove unreacted indene and then to isolate the desired product, 1-benzyldimethylsilylindene (6.2 g, ~92% yield).

Example 2a: Complex with 1-tribenzylsilylindenyl Ligand

Under Ar, 15 mL of a hexane solution of the compound prepared in Example 1a (0.627 g, 1.5 mmol) was dropwise added to 15 mL of a solution of 1.00 g (1.6 mmol) Gd(III) {N[Si(CH_3)_3]_2}_3 (hereinafter "Gd[N(TMS)_2]_3") in hexane. This mixture was stirred at 80° C. overnight (~14 hours), during which time a yellow solution formed.

The reaction vessel was cooled to room temperature before all volatiles were removed under vacuum.

The product recovered was 1.34 g (~100% yield) of an off-white crystalline solid having the following structure:

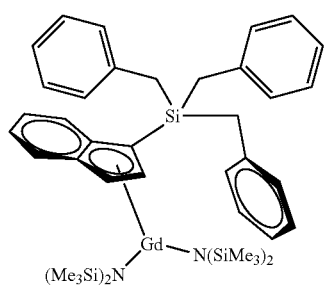

(IIa)

Example 2b: Complex with 1-benzyldimethylsilylindenyl Ligands

Under Ar, to a 30 mL solution of the compound prepared in Example 1b (1.22 g, 4.6 mmol) and 1.50 g (2.35 mmol) Gd[N(TMS)_2]_3 in hexane was slowly added 2.22 mL 1,1,3,3-tetramethyldisilazane (1.25 g, 12.5 mmol). A small amount of white precipitate formed quickly.

This mixture was stirred at 80° C. overnight (~14 hours) before the pale yellow solution was transferred to a flask under Ar. Solvent was removed under vacuum, resulting in the recovery of 1.92 g (~100% yield) of, as a pale yellow oil:

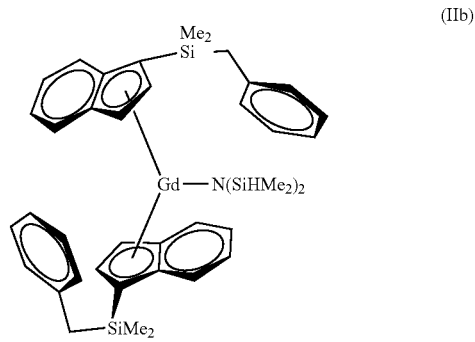

(IIb)

Example 2c: Complex with 1-tert-butyldimethylsilylindenyl Ligands

Under Ar, to a 30 mL solution of 1-tert-butyldimethylsilylindene (1.415 g, 6.1 mmol) and 2.00 g (3.1 mmol) Gd[N(TMS)_2]_3 in hexane was slowly added 2.22 mL 1,1,3,3-tetramethyldisilazane (1.67 g, 12.5 mmol). A small amount of white precipitate formed quickly.

This mixture was stirred at 80° C. overnight (~14 hours) before the orange solution was transferred to a flask under Ar. Solvent was removed under vacuum, resulting in the recovery of 2.30 g (~93% yield) of, as a red oil:

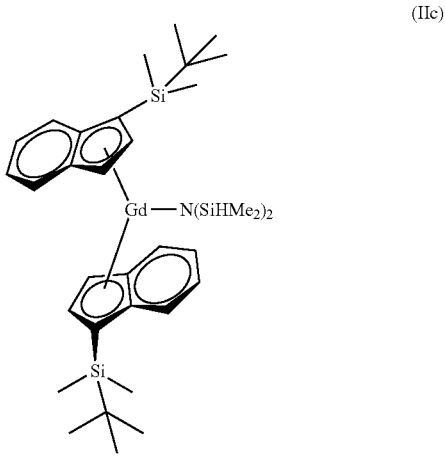

(IIc)

Example 2d: Complex with 1,3-bis(tert-butyldimethylsilyl)indenyl Ligands

The reaction from Example 2c was repeated except that 2.116 g (6.1 mmol) 1,3-bis(tert-butyldimethylsilyl)indene was used in place of 1-tert-butyldimethylsilylindene.

This mixture was stirred at 80° C. overnight (~12 hours) before the pale yellow solution was transferred to a flask under Ar. Solvent was removed under vacuum, resulting in the recovery of 3.00 g (~100% yield) of, as a yellow oil:

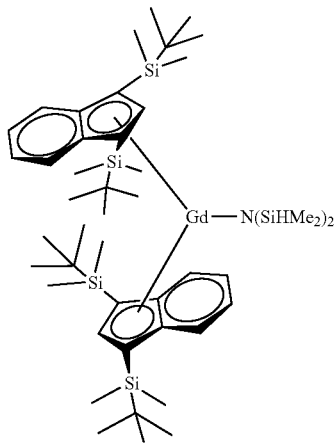

(IId)

Example 2e: Complex with
1,3-bis(trimethylsilyl)indenyl Ligands

The process from Example 2d was repeated except that 1.600 g (6.1 mmol) 1,3-bis(trimethylsilyl)indene was used in place of 1,3-bis(tert-butyldimethylsilyl)indene. The product recovered was 2.46 g (~99% yield) of, as a yellow oil:

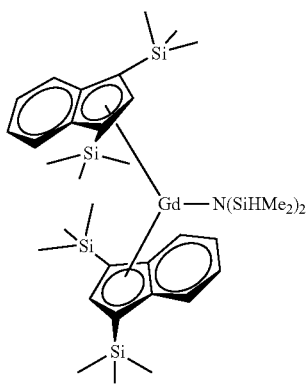

(IIe)

Examples 2f-2h: Additional Complexes

Using procedures similar to those described above, the following additional complexes also were prepared:

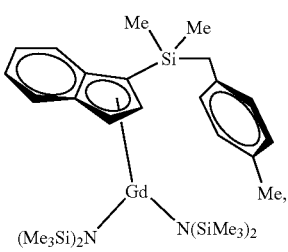

(IIf)

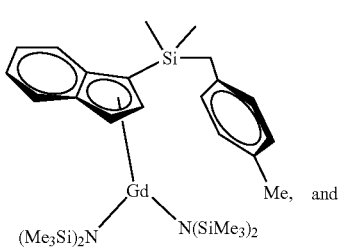

(IIg)

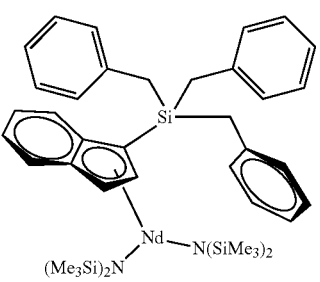

(IIh)

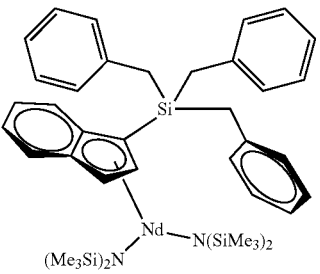

Each of the complexes from Examples 2a-2h was used to prepare a catalyst for at least one polymerization of butadiene and ethylene.

To assist in comparing the effects of the complexes as catalyst components, the monomers that underwent polymerization and many other variables were held constant; however, this should not be considered to be limiting. Monoethylenically unsaturated monomers (e.g., α-olefins) other than ethylene and polyenes other than butadiene certainly can be used alternatively or additionally. Other parameters of the polymerization also can be changed.

Examples 3-7: Copolymerizations Using Formula (IIa) Complex-Containing Catalysts Except as noted below, the following procedure was used in each of the polymerizations.

To a dry, $N_2$-purged stainless steel 5 L vessel was added dry solvent (1.80 kg toluene or 1.77 kg hexane—see Table 1) and varying amounts (see Table 1) of purified, dry 1,3-butadiene before the reactor was pressurized to 0.2 MPa with ethylene. The reactor agitator was initiated, the jacket was heated to 50° C., and the reactor contents were allowed to equilibrate to that temperature.

During equilibration, a 200 mL bottle that was previously dried and $N_2$-purged was placed in an Ar glovebox. To this bottle was added 50 mL dry solvent followed by varying amounts (see Table 1 below) of a 1.02±0.05 M solution of DIBAH in solvent, formula II(a) complex, and finally varying amounts (see Table 1 below) of either:
  (1) where toluene was used as solvent, varying amounts of solid N,N-dimethylanilinium tetra(pentafluorophenyl)borate (DEATPFPB), or
  (2) where hexane was used as solvent, varying amounts of a 0.0326 M solution of di(octadecyl)methylammonium tetrakis(pentafluorophenyl)borate in cyclohexane.

The mixture was sealed and removed from the glovebox.

The contents of the small bottle were injected into the reactor, and gaseous dried ethylene was allowed to fill the reactor to a final pressure of 1.72 MPa. The jacket temperature of the reactor was increased (see Table 1 below).

After varying amounts of time (see Table 1 below), each polymer cement was dropped into a vat of 2-propanol containing 2,6-di-tert-butyl-4-methylphenol.

Recovered polymer was drum dried at 120° C.

The amounts of polymer, mer content and other properties also are summarized below in Table 1. Mole percentages were calculated from $^1$H and $^{13}$C NMR spectroscopic data, while molecular weight information was determined by high temperature GPC.

TABLE 1

Catalyst information and polymer properties, formula (IIa)-type complex

|  | 3 | 4 | 5 | 6 | 7 |
|---|---|---|---|---|---|
| Amt. of complex, mmol | 0.045 | 0.045 | 0.045 | 0.138 | 0.138 |
| Amt. borate, mmol | 0.0473 | 0.0473 | 0.0473 | 0.145 | 0.145 |
| Amt. DIBAH, mmol | 3.6 | 3.6 | 1.8 | 6.1 | 3.0 |
| Catalyst aging time (min.) | 20 | 20 | 15 | 0 | 0 |
| Solvent | toluene | toluene | toluene | hexane | hexane |
| Amt. 1,3-BD (g), reactor | 200 | 200 | 200 | 230 | 230 |
| Polymerization temp. (° C.) | 80 | 120 | 100 | 100 | 100 |
| Polymerization time, min. | 120 | 50 | 180 | 122 | 180 |
| Amt. of polymer, g | 295 | 221 | 148 | 236 | 288 |
| ethylene mer, mol % | 47.3 | 44.5 | 55.9 | 53.7 | 67.2 |
| butadiene mer, mol % | 52.7 | 55.5 | 44.1 | 46.3 | 32.8 |
| cis-1,4 BD mer, % | 57.8 | 51.2 | 92.1$^a$ | 94.7$^a$ | 91.6$^a$ |
| trans-1,4 BD mer, % | 38.1 | 44.3 |  |  |  |
| 1,2-vinyl BD mer, % | 4.1 | 4.5 | 7.9 | 5.3 | 8.4 |
| isolated BD mer, % | 32 | 29 | 60 | 48 | 79 |
| $M_n$ (kg/mol) | 43.3 | 49.5 | 101.8 | 53.1 | 73.9 |
| $M_w/M_n$ | 7.3 | 4.7 | 5.8 | 12.6 | 10.2 |
| 1st $T_m$ (° C.) | 52.4 | 47.9 | −16.8 | 18.3 | 15.5 |
| 2nd $T_m$ (° C.) | n/a | n/a | 16.1 | 46.2 | 45.3 |
| 3rd $T_m$ (° C.) | n/a | n/a | 46.7 | n/a | n/a |

$^a$Isomerism not determined, with combined amount of mer having 1,4-microstructure listed in table.

A 6.05 mg portion of the polymer from Example 3 was tested by DSC over a temperature range of −150° to ~200° C., the results of which are shown in FIG. 1. The presence of a melting point indicates that the interpolymer includes a block (i.e., is not fully alternating or random), its location on the curve (T≈50° C.) tends to suggest that the block contains both butadiene and ethylene mer, and its broad nature suggests mer randomness and asymmetry. (Blocks that are all (or essentially all) butadiene mer have a $T_m$≈−15° C., while blocks that are all (or essentially all) ethylene mer have a $T_m$≈120° C. In each case, the "approximately equal" symbol should be read as a range of 5-10° C. on each side of the stated value.)

Other portions of the polymer from Example 3 were dissolved in deuterated tetrachloroethane and subjected to NMR spectroscopy, using the settings shown below:

TABLE 2

NMR spectrometer settings

|  | $^1$H | $^{13}$C |
|---|---|---|
| Sample temp. (° C.) | 120 | 120 |
| Acquisition time (sec) | 4.0 | 2.0 |
| Frequency (MHz) | 300.06 | 75.46 |
| Spectrum offset (Hz) | 1796.60 | 7907.60 |
| Sweep width (Hz) | 4803.07 | 18115.94 |
| Receiver gain | 24.0 | 30.0 |

Figure 2:
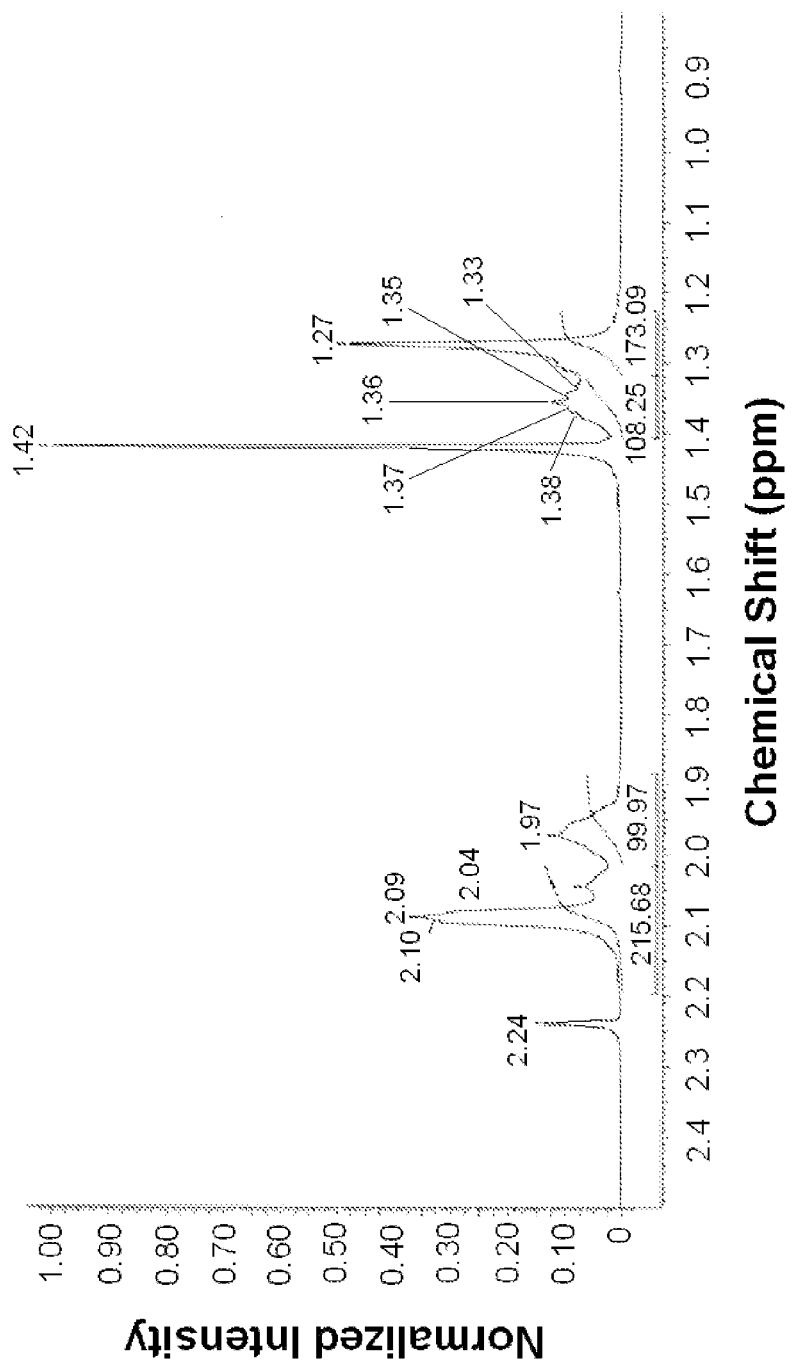
FIG. 2 is proton nuclear magnetic resonance (NMR) spectrograph of the polymer from Example 3.

The $^1$H NMR spectrograph is shown in FIG. 2. The peak centered at a chemical shift of ~1.95-1.97 ppm is believed to represent so-called isolated butadiene mer, i.e., butadiene mer that is not part of a block or microblock of butadiene mer and, instead, sandwiched by ethylene mer.

Figure 3:
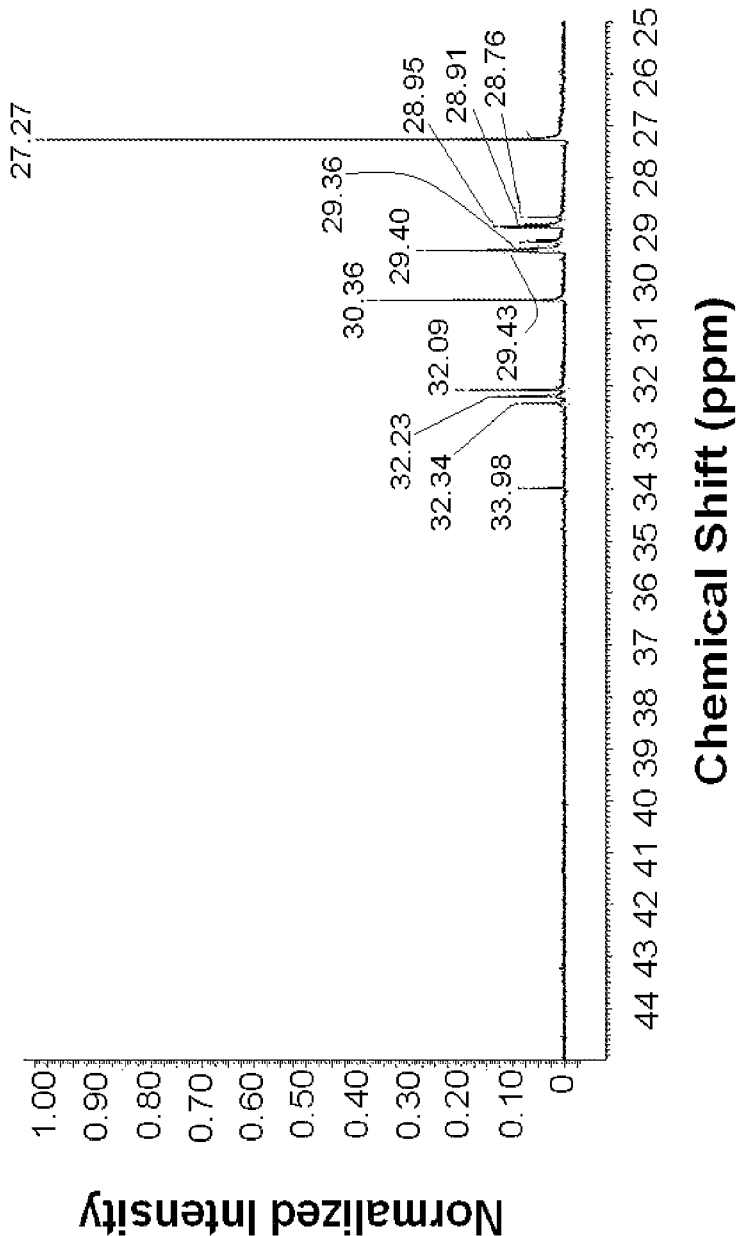
FIG. 3 is $^{13}C$ NMR spectrograph of the polymer from Example 3.

The $^{13}$C NMR spectrograph is shown in FIG. 3. The peaks centered at chemical shifts of ~32.1 and ~32.2 ppm are believed to represent the presence of the same isolated butadiene mer discussed in the preceding paragraph.

(The integrations of the noted peaks from these NMR spectrographs relative to the sum of integrations of all peaks attributable to butadiene mer were used to calculate the isolated butadiene mer in Table 1 above.)

Examples 8-15: Copolymerizations Using Catalysts Containing Formula (IIb)-(IIe) Complexes The process from Examples 3-7 was essentially repeated except as noted below.

The polymerization of Example 10 was modified by including 0.25 g 1,3-butadiene to the catalyst composition bottle prior to addition of the DIBAH solution.

The polymerizations of Examples 13 and 15 employed 5.78 mL of 1.05 M solution of DIBAH in hexane and 4.45 mL of a 0.0326 M di(octadecyl)methylammonium tetrakis (pentafluorophenyl)borate solution in cyclohexane was used rather than the DEATPFPB solution.

Conditions and polymer properties are summarized below in Table 3.

TABLE 3

Catalyst information and polymer properties

|  | 8 | 9 | 10 | 11 | 12 | 13 | 14 | 15 |
|---|---|---|---|---|---|---|---|---|
| complex | (IIb) | (IIb) | (IIb) | (IIc) | (IId) | (IId) | (IIe) | (IIe) |
| Amt. of complex, mmol | 0.045 | 0.045 | 0.045 | 0.045 | 0.045 | 0.045 | 0.138 | 0.138 |

TABLE 3-continued

Catalyst information and polymer properties

|  | 8 | 9 | 10 | 11 | 12 | 13 | 14 | 15 |
|---|---|---|---|---|---|---|---|---|
| Amt. borate, mmol | 0.0473 | 0.0473 | 0.0473 | 0.0473 | 0.0473 | 0.0473 | n/a | n/a |
| Amt. DIBAH, mmol | 3.6 | 3.6 | 3.6 | 3.6 | 3.6 | 6.1 | 3.9 | 6.1 |
| Catalyst aging time (min.) | 20 | 20 | 60 | 20 | 20 | 0 | 20 | 0 |
| Solvent | toluene | toluene | toluene | toluene | toluene | hexane | toluene | hexane |
| Amt. 1,3-BD (g), reactor | 200 | 200 | 200 | 200 | 200 | 230 | 216 | 230 |
| Polymerization temp. (° C.) | 80 | 80 | 80 | 80 | 80 | 80 | 80 | 80 |
| Polymerization time, min. | 120 | 180 | 180 | 120 | 120 | 120 | 120 | 120 |
| Amt. of polymer, g | 100 | 282 | 291 | 240 | 220 | 245 | 232 | 235 |
| ethylene mer, mol % | 39.5 | 47.5 | 53.9 | 27.9 | 21.2 | 26.5 | 23.5 | 17.5 |
| butadiene mer, mol % | 60.5 | 52.5 | 46.1 | 72.1 | 78.8 | 73.5 | 76.5 | 82.5 |
| cis-1,4 BD mer, % | 48.7 | 58.9 | 46.1 | 98.2[b] | 97.1[b] | 96.4[b] | 97.8[b] | 97.1[b] |
| trans-1,4 BD mer, % | 43.9 | 35.8 | 48.1 | | | | | |
| 1,2-vinyl BD mer, % | 7.4 | 5.3 | 5.8 | 1.8 | 2.9 | 3.6 | 2.2 | 2.9 |
| isolated BD mer, % | 42 | 34 | 46 | <1 | <1 | <1 | <1 | 5 |
| $M_n$ (kg/mol) | 64.4 | 81.2 | 61.6 | 76.2 | 59.5 | 34.9 | 61.5 | 39.6 |
| $M_w/M_n$ | 13.5 | 11.2 | 12.6 | 10.2 | 7.3 | 10.6 | 8.3 | 13.0 |
| 1st $T_m$ (° C.) | −12.6 | −15.2 | −15.2 | −11.5 | −13.2 | −14.0 | −10.9 | −12.7 |
| 2nd $T_m$ (° C.) | 16.8 | 40.7 | 17.6 | 121.4 | 124.4 | 117.4 | 124.4 | 114.8 |
| 3rd $T_m$ (° C.) | 43.8 | n/a | 42.8 | n/a | n/a | n/a | n/a | n/a |

[b]Isomerism not determined, with combined amount of mer having 1,4-microstructure listed in table.

Portions of the polymers from Examples 8-10 were tested by DSC over a temperature range of −150° to ~200° C. The presence of multiple melting points indicated the possible presence of multiple blocks, with a peak at T≈−15° C. suggesting a block of butadiene mer and a peak at T≈40°-45° C. suggesting a block that contains both butadiene and ethylene mer. The amount of isolated butadiene mer for each of these polymers (see Table 3 above) might suggest that this latter black includes randomly distributed, if not alternating, mer.

Examples 16-20: Copolymerizations Using Formula (IIf) Complex-Containing Catalysts The process from Examples 3-7 was essentially repeated. Conditions and polymer properties are summarized below in Table 4.

TABLE 4

Catalyst information and polymer properties, formula (IIf)-type complex

|  | 16 | 17 | 18 | 19 | 20 |
|---|---|---|---|---|---|
| Amt. of complex, mmol | 0.138 | 0.138 | 0.138 | 0.045 | 0.060 |
| Amt. borate, mmol | 0.145 | 0.145 | 0.145 | 0.0473 | 0.063 |
| Amt. DIBAH, mmol | 6.1 | 6.1 | 3.0 | 3.6 | 3.0 |
| Catalyst aging time (min.) | 0 | 0 | 0 | 15 | 15 |
| Solvent | hexane | hexane | hexane | toluene | toluene |
| Amt. 1,3-BD (g), reactor | 230 | 230 | 230 | 200 | 200 |
| Polymerization temp. (° C.) | 100 | 100 | 100 | 85 | 85 |
| Polymerization time, min. | 120 | 180 | 244 | 180 | 240 |
| Amt. of polymer, g | 196 | 392 | 215 | 126 | 288 |
| ethylene mer, mol % | 61.3 | 65.8 | 63.7 | 56.8 | 51.7 |
| butadiene mer, mol % | 30.7 | 34.2 | 36.3 | 43.2 | 48.3 |
| 1,4 BD mer, % | 93.7 | 93.9 | 93.5 | 91.1 | 94.3 |
| 1,2-vinyl BD mer, % | 6.3 | 6.1 | 6.5 | 8.9 | 5.7 |
| isolated BD mer, % | 80 | 85 | 83 | 70 | 86 |
| $M_n$ (kg/mol) | 43.9 | 47.6 | 72.8 | 63.7 | 82.3 |
| $M_w/M_n$ | 6.4 | 8.5 | 7.9 | 4.0 | 4.0 |
| 1st $T_m$ (° C.) | 15.3 | 17.0 | 17.4 | −15.0 | −15.2 |
| 2nd $T_m$ (° C.) | 47.9 | 50.0 | 51.2 | 31.2 | 32.0 |
| 3rd $T_m$ (° C.) | n/a | n/a | n/a | 97.7 | 44.5 |

In the polymer from Example 19, the presence of a melting point at T≈100° C. suggests the presence of a block of ethylene mer.

Figure 4:
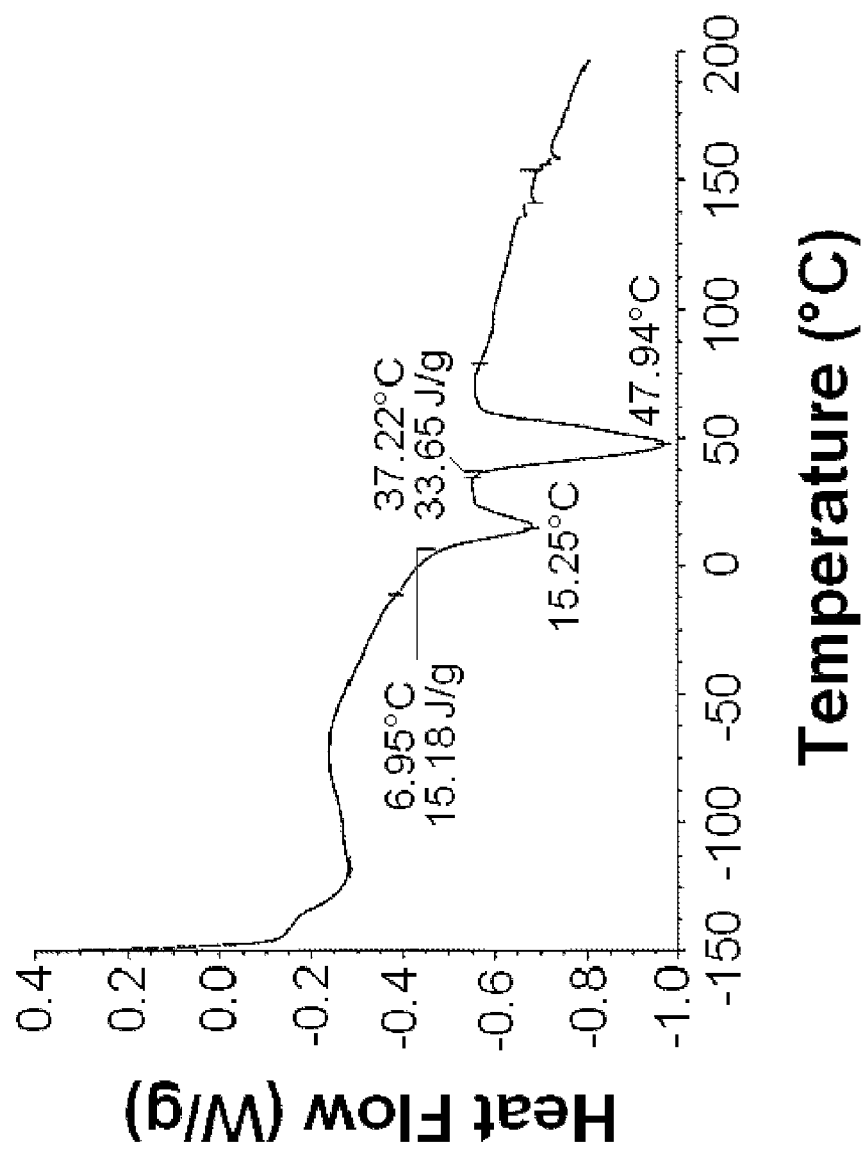
FIG. 4 is a heat flow vs. temperature DSC plot on the polymer from Example 16.

A DSC plot over a temperature range of −150° to ~200° C. for a 3.83 mg sample of the polymer of Example 16 is shown in FIG. 4. The presence of distinct melting points indicates that the interpolymer includes blocks, and the location of the second one on the curve (T≈45°-50° C.) tends to suggest a block that contains both butadiene and ethylene mer.

Other portions of the polymer from Example 16 were dissolved in deuterated tetrachloroethane and subjected to NMR spectroscopy, using the settings shown below:

TABLE 5

NMR spectrometer settings

|  | $^1$H | $^{13}$C |
|---|---|---|
| Sample temp. (° C.) | 120 | 120 |
| Acquisition time (sec) | 2.0 | 2.0 |
| Frequency (MHz) | 300.06 | 75.46 |
| Spectrum offset (Hz) | 1796.60 | 7907.02 |
| Sweep width (Hz) | 4803.07 | 18115.94 |
| Receiver gain | 22.0 | 30.0 |

Figure 5:
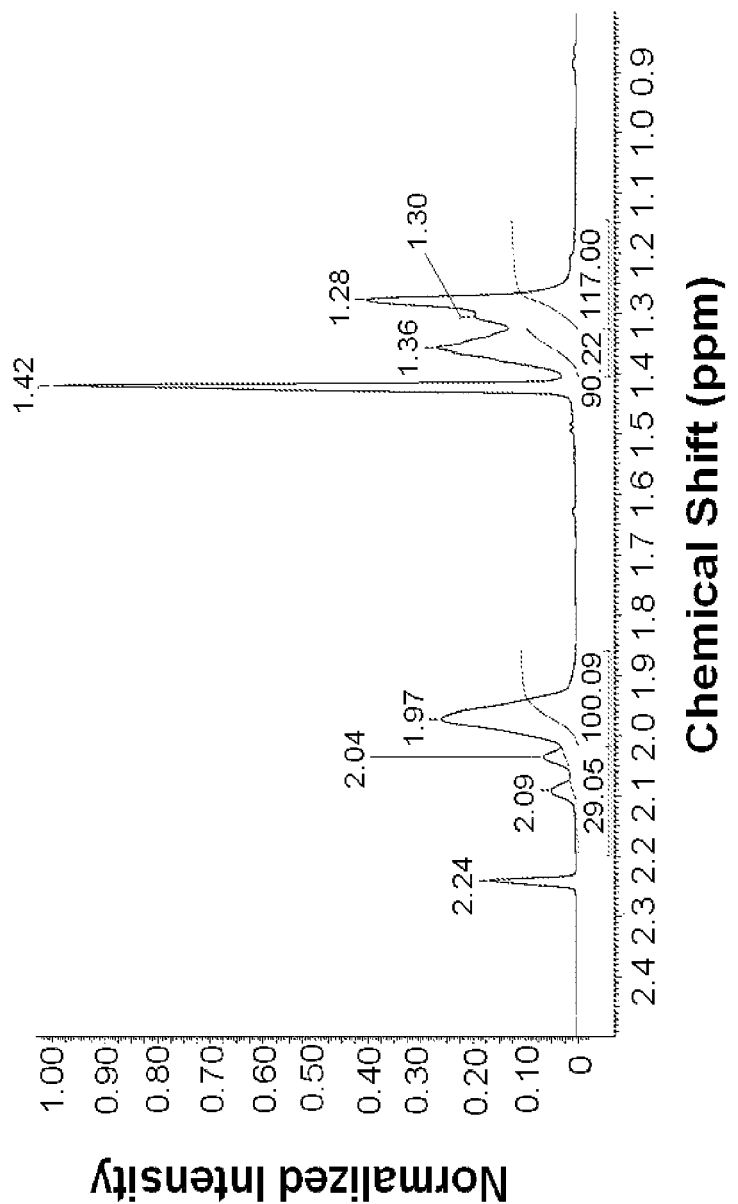
FIG. 5 is $^1H$ NMR spectrograph of the polymer from Example 16.
Figure 6:
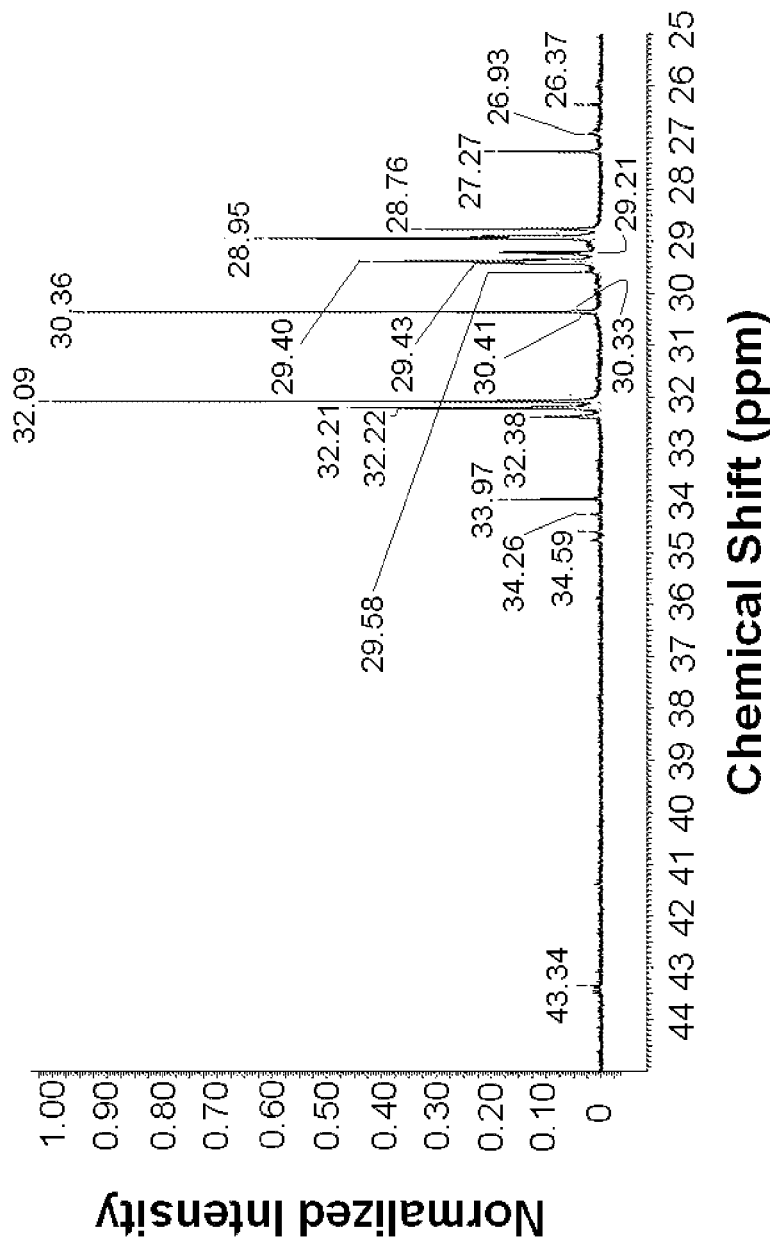
FIG. 6 is $^{13}C$ NMR spectrograph of the polymer from Example 16.

The $^1$H NMR and $^{13}$C NMR spectrographs are shown in, respectively, FIGS. 5 and 6. The large peaks at approximately the same chemical shifts discussed above in connection with FIGS. 2 and 3 are believed to indicate an extremely high level of isolated butadiene mer.

Examples 21-22: Copolymerizations Using Formula (IIg) Complex-Containing Catalysts The process from Examples 3-7 was essentially repeated.
Conditions and polymer properties are summarized below in Table 6.

TABLE 6

Catalyst information and polymer properties, formula (IIg)-type complex

|  | 21 | 22 |
|---|---|---|
| Amt. of complex, mmol | 0.045 | 0.138 |
| Amt. borate, mmol | 0.0473 | 0.145 |
| Amt. DIBAH, mmol | 3.6 | 6.1 |
| Catalyst aging time (min.) | 20 | 0 |
| Solvent | toluene | hexane |
| Amt. 1,3-BD (g), reactor | 200 | 230 |
| Polymerization temp. (° C.) | 80 | 100 |
| Polymerization time, min. | 60 | 120 |
| Amt. of polymer, g | 256 | 367 |
| ethylene mer, mol % | 49.2 | 63.3 |
| butadiene mer, mol % | 50.8 | 36.7 |
| 1,4 BD mer, % | 95.0 | 94.4 |
| cis configuration, % | x | 12.1 |
| trans configuration, % | x | 82.2 |
| 1,2-vinyl BD mer, % | 5.0 | 5.6 |
| isolated BD mer, % | 37 | 75 |
| $M_n$ (kg/mol) | 32.1 | 45.9 |
| $M_w/M_n$ | 16.3 | 7.8 |
| 1st $T_m$ (° C.) | −16.2 | 12.5 |
| 2nd $T_m$ (° C.) | 19.4 | 47.0 |
| 3rd $T_m$ (° C.) | 43.8 | 107.0 |
| 4th $T_m$ (° C.) | 107.6 | n/a |

In both of the polymers, the presence of a melting point at T>100° C. suggests the presence of a block of ethylene mer.

Examples 23-25: Copolymerizations Using Formula (IIh) Complex-Containing Catalysts The process from Examples 3-7 again was essentially repeated.

Conditions and polymer properties are summarized below in Table 7.

TABLE 7

Catalyst information and polymer properties, formula (IIh)-type complex

|  | 23 | 24 | 25 |
|---|---|---|---|
| Amt. of complex, mmol | 0.045 | 0.138 | 0.138 |
| Amt. borate, mmol | 0.0473 | 0.210 | 0.145 |
| Amt. DIBAH, mmol | 3.6 | 6.1 | 6.1 |
| Catalyst aging time (min.) | 20 | 0 | 0 |
| Solvent | toluene | hexane | hexane |
| Amt. 1,3-BD (g), reactor | 200 | 230 | 230 |
| Polymerization temp. (° C.) | 100 | 100 | 100 |
| Polymerization time, min. | 135 | 240 | 330 |
| Amt. of polymer, g | 95 | 164 | 244 |
| ethylene mer, mol % | 39.5 | 47.5 | 51.0 |
| butadiene mer, mol % | 60.5 | 52.5 | 49.0 |
| 1,4 BD mer, % | 94.3 | 94.2 | 94.3 |
| 1,2-vinyl BD mer, % | 5.7 | 5.8 | 5.7 |
| isolated BD mer, % | 59 | 82 | 86 |
| $M_n$ (kg/mol) | 99.2 | 43.0 | 48.0 |
| $M_w/M_n$ | 3.7 | 8.7 | 9.2 |
| 1st $T_m$ (° C.) | 32.3 | 31.3 | 50.2 |
| 2nd $T_m$ (° C.) | 47.3 | 43.7 | n/a |
| 3rd $T_m$ (° C.) | n/a | 100.4 | n/a |

Figure 7:
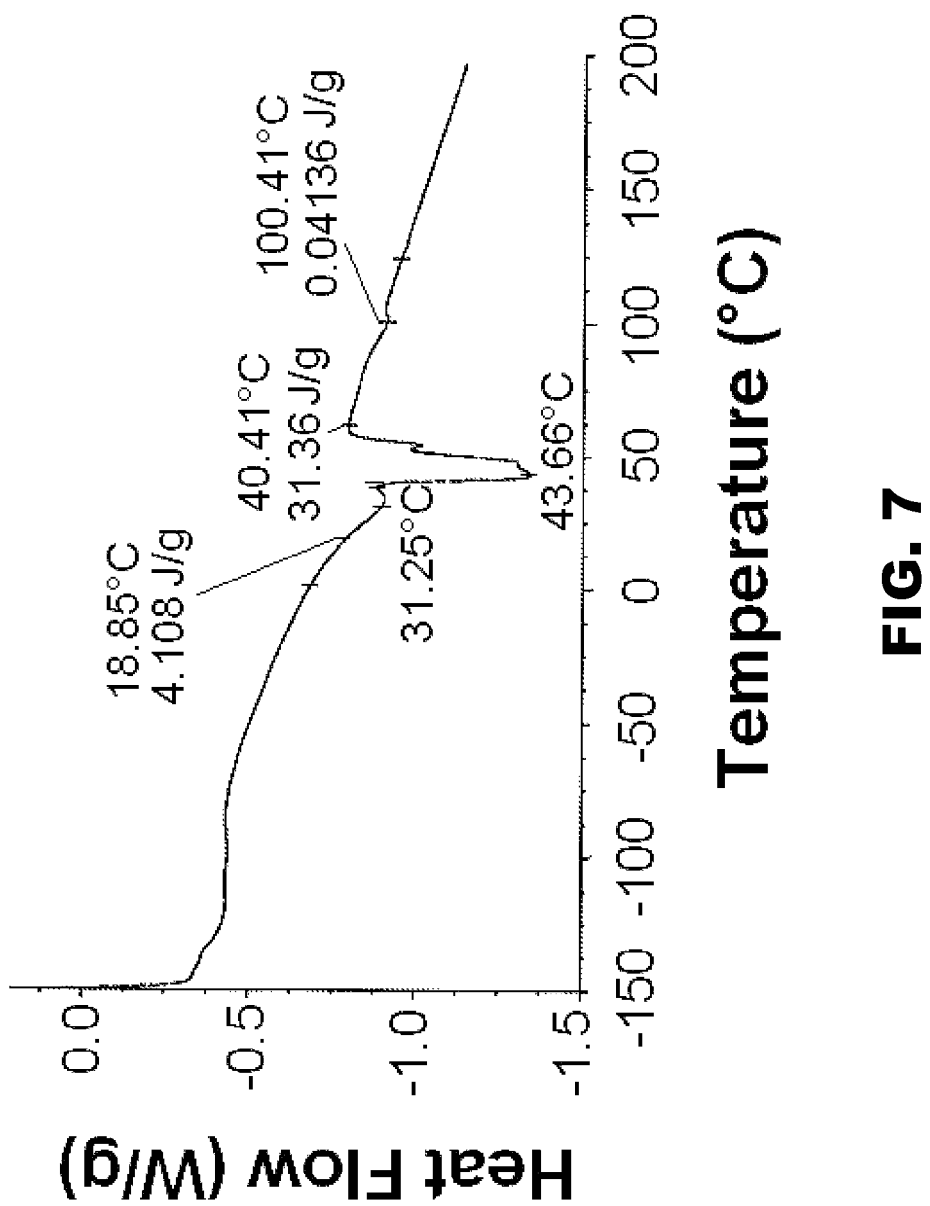
FIG. 7 is a heat flow vs. temperature DSC plot on the polymer from Example 24.

A DSC plot over a temperature range of −150° to ~200° C. for a 4.08 mg sample of the polymer of Example 24 is shown in FIG. 7. The presence of a relatively broad melting point at T≈40°-60° C. indicates a block that contains both butadiene and ethylene mer, likely one that involves significant randomness and, perhaps, asymmetry.

Other portions of the polymer from Example 24 were dissolved in deuterated tetrachloroethane and subjected to NMR spectroscopy, using the settings shown below:

TABLE 8

NMR spectrometer settings

|  | $^1$H | $^{13}$C |
|---|---|---|
| Sample temp. (° C.) | 120 | 120 |
| Acquisition time (sec) | 2.0 | 2.0 |
| Frequency (MHz) | 300.06 | 75.46 |
| Spectrum offset (Hz) | 1796.60 | 7907.44 |
| Sweep width (Hz) | 4803.07 | 18115.94 |
| Receiver gain | 28.0 | 30.0 |

Figure 8:
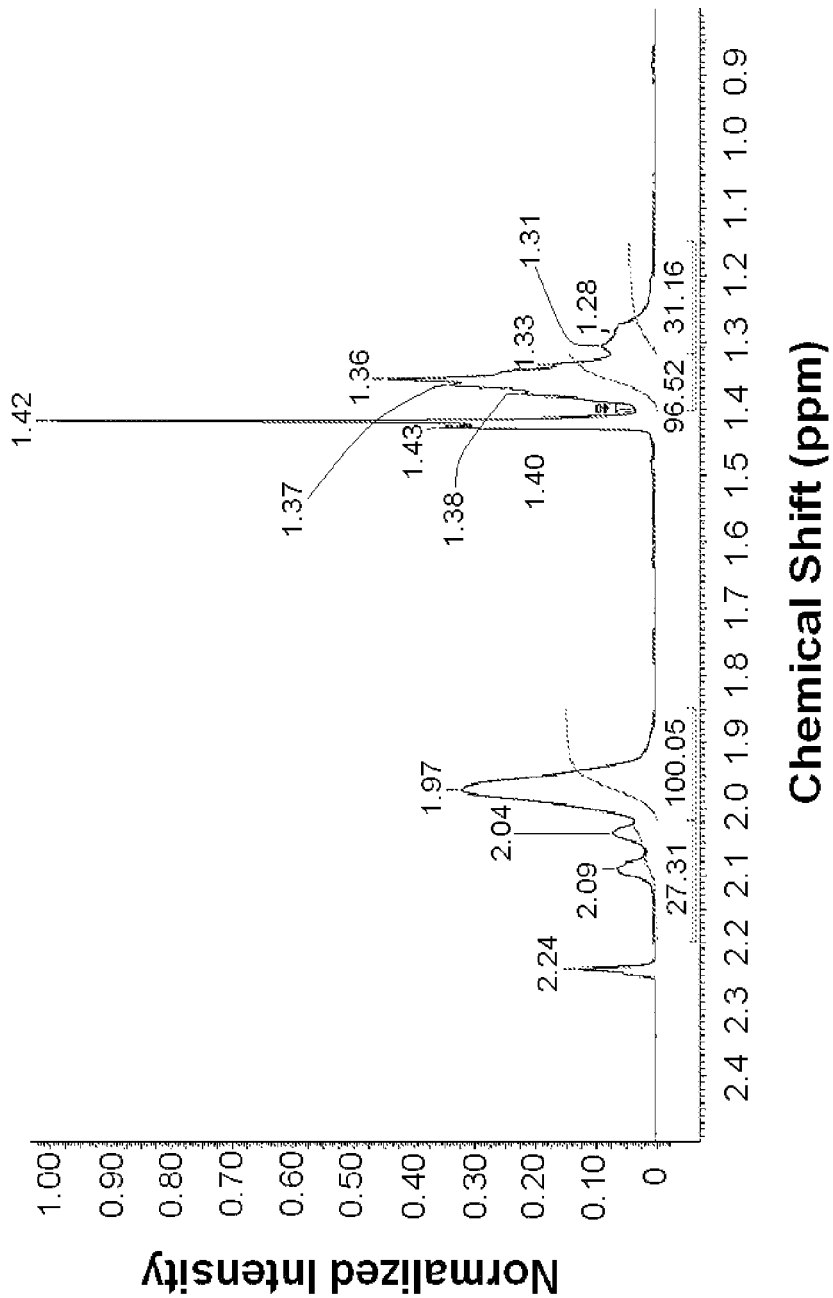
FIG. 8 is $^1H$ NMR spectrograph of the polymer from Example 24.
Figure 9:
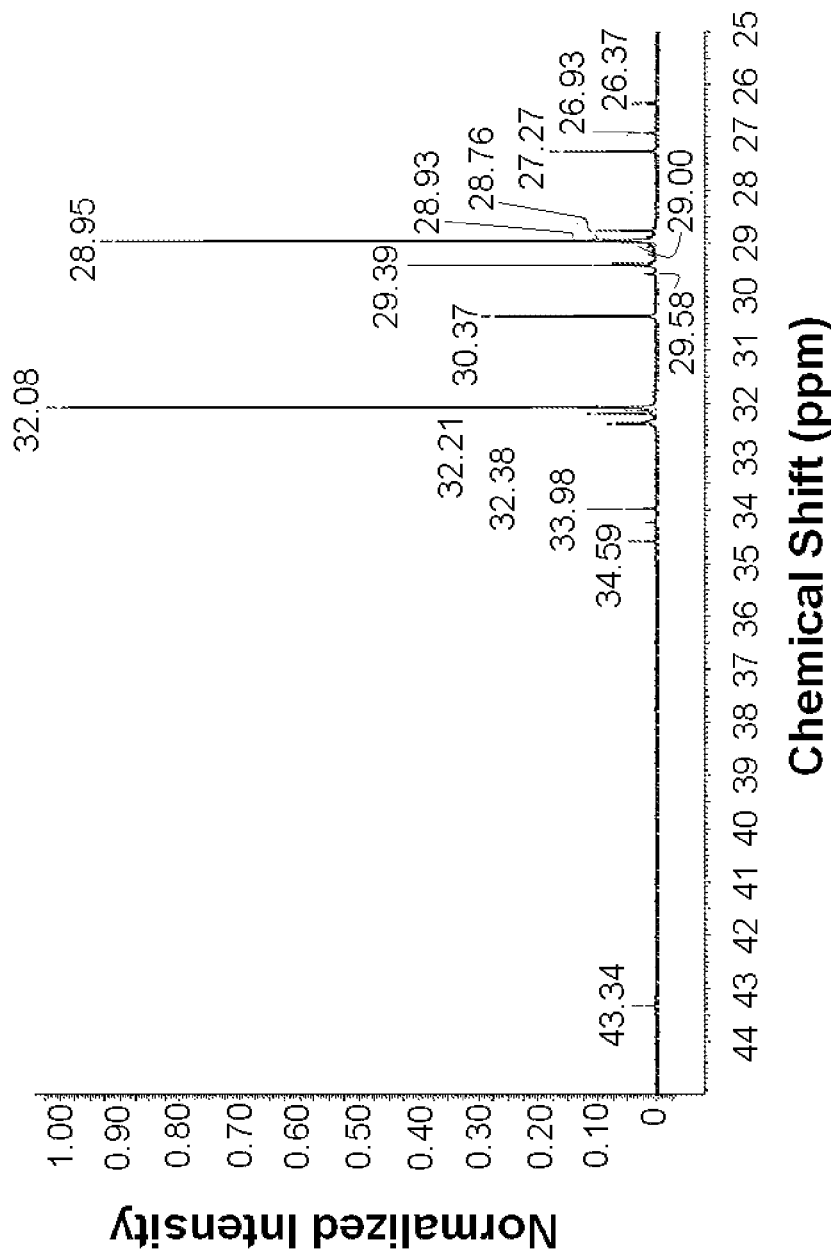
FIG. 9 is $^{13}C$ NMR spectrograph of the polymer from Example 24.

The $^1$H NMR and $^{13}$C NMR spectrographs are shown in, respectively, FIGS. 8 and 9. The large peaks at approximately the same chemical shifts discussed above in connection with FIGS. 2 and 3 are believed to indicate an extremely high level of isolated butadiene mer.

That which is claimed is:

1. A catalyst composition useful for polymerizing mixtures of polyene and α-olefin mer, said composition comprising a complex defined by the general formula

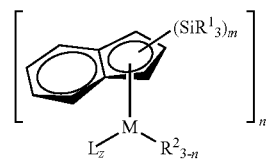

where
  M represents a Group 3 metal atom;
  L represents a neutral Lewis base;
  z is an integer of from 0 to 3 inclusive;
  m is 1 or 2 with the proviso that, when m is 2, the silyl groups are at the 1 and 3 positions of the indenyl ligand;
  n is 1 or 2;
  each $R^1$ independently is a $C_1$-$C_{20}$ alkyl group or a —$(CH_2)R^3$ group with $R^3$ being a phenyl group optionally substituted with an alkyl group, with the proviso that at least one $R^1$ is —$(CH_2)R^3$; and
  $R^2$ is an X-type, monoanionic ligand,
wherein, when z is not zero, one L group and one $R^2$ group can join so as to provide, together with the M atom to which each is bonded, a cyclic moiety.

2. The catalyst composition of claim 1 wherein z of said complex is 0.

3. The catalyst composition of claim 1 wherein M of said complex is a lanthanide metal atom.

4. The catalyst composition of claim 1 wherein m of said complex is 1, said silyl group being bonded at the 1-position of the indenyl ligand.

5. A process for providing a polymer, said process comprising contacting one or more ethylenically unsaturated hydrocarbons with the catalyst composition of claim 1 and allowing said polymer to form therefrom, said process optionally further comprising reacting said polymer with a functionalizing agent so as to provide terminal functionality to said polymer.

6. The process of claim 5 wherein said one or more ethylenically unsaturated hydrocarbons comprises at least one conjugated diene compound.

7. The process of claim 6 wherein said one or more ethylenically unsaturated hydrocarbons further comprises at least one α-olefin.

8. The process of claim 7 wherein at least 50 mole percent of the conjugated diene mer are incorporated in 1,4-cis configuration.

9. The process of claim 8 wherein said polymer comprises at least one block of conjugated diene mer and at least one block of randomly distributed conjugated diene and α-olefin mer.

10. The catalyst composition of claim 1 wherein each $R^1$ independently is a —$(CH_2)R^3$ group with $R^3$ being a phenyl group optionally substituted with an alkyl group.

11. A catalyst composition useful for polymerizing mixtures of polyene and α-olefin mer, said composition comprising a complex defined by the general formula

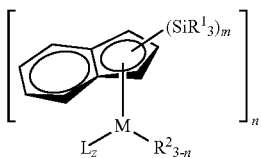

where
   M represents a Group 3 metal atom;
   L represents a neutral Lewis base;
   z is an integer of from 0 to 3 inclusive;
   m is 1 or 2 with the proviso that, when m is 2, the silyl groups are at the 1 and 3 positions of the indenyl ligand;
   n is 2;
   each $R^1$ independently is a $C_1$-$C_{20}$ alkyl group or a —$(CH_2)R^3$ group with $R^3$ being a phenyl group optionally substituted with an alkyl group, with the proviso that at least one $R^1$ is —$(CH_2)R^3$; and
   $R^2$ is an X-type, monoanionic ligand,
wherein, when z is not zero, one L group and one $R^2$ group can join so as to provide, together with the M atom to which each is bonded, a cyclic moiety.

12. The catalyst composition of claim 11 wherein z of said complex is 0.

13. The catalyst composition of claim 11 wherein M of said complex is a lanthanide metal atom.

14. The catalyst composition of claim 11 wherein each $R^1$ independently is a —$(CH_2)R^3$ group with $R^3$ being a phenyl group optionally substituted with an alkyl group.

15. The catalyst composition of claim 11 wherein m of said complex is 1, said silyl group being bonded at the 1-position of the indenyl ligand.

16. A catalyst composition useful for polymerizing mixtures of polyene and α-olefin mer, said composition comprising a complex defined by the general formula

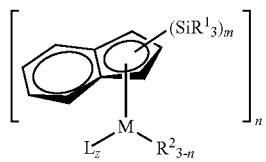

where
   M represents a lanthanide metal atom;
   L represents a neutral Lewis base;
   z is an integer of from 0 to 3 inclusive;
   m is 1, in which case the silyl group is bonded at the 1-position of the indenyl ligand, or 2, in which case the silyl groups are at the 1 and 3 positions of the indenyl ligand;
   n is 2;
   each $R^1$ independently is a $C_1$-$C_{20}$ alkyl group or a —$(CH_2)R^3$ group with $R^3$ being a phenyl group optionally substituted with an alkyl group, with the proviso that at least one $R^1$ is —$(CH_2)R^3$; and
   $R^2$ is an X-type, monoanionic ligand,
wherein, when z is not zero, one L group and one $R^2$ group can join so as to provide, together with the M atom to which each is bonded, a cyclic moiety.

17. The catalyst composition of claim 16 wherein z of said complex is 0.

18. The catalyst composition of claim 16 wherein each $R^1$ independently is a —$(CH_2)R^3$ group with $R^3$ being a phenyl group optionally substituted with an alkyl group.

\* \* \* \* \*